United States Patent
Podack et al.

(10) Patent No.: US 9,499,627 B2
(45) Date of Patent: *Nov. 22, 2016

(54) METHOD FOR IN VIVO EXPANSION OF T REGULATORY CELLS

(75) Inventors: Eckhard R. Podack, Coconut Grove, FL (US); Taylor Schreiber, North Bay Village, FL (US); Dietlinde-Maria Wolf, Key Biscayne, FL (US)

(73) Assignee: University of Miami, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/388,722

(22) PCT Filed: Aug. 3, 2010

(86) PCT No.: PCT/US2010/044218
§ 371 (c)(1),
(2), (4) Date: Feb. 3, 2012

(87) PCT Pub. No.: WO2011/017303
PCT Pub. Date: Feb. 10, 2011

(65) Prior Publication Data
US 2012/0135011 A1 May 31, 2012

Related U.S. Application Data

(60) Provisional application No. 61/273,299, filed on Aug. 3, 2009.

(51) Int. Cl.
| | | |
|---|---|---|
| *C07K 14/52* | (2006.01) |
| *C07K 14/525* | (2006.01) |
| *C07K 16/28* | (2006.01) |
| *A61K 38/19* | (2006.01) |
| *A61K 39/395* | (2006.01) |
| *C07K 14/705* | (2006.01) |
| *C07K 14/715* | (2006.01) |
| *A61K 38/17* | (2006.01) |
| *A61K 39/00* | (2006.01) |

(52) U.S. Cl.
CPC ........... *C07K 16/2878* (2013.01); *A61K 38/17* (2013.01); *A61K 38/19* (2013.01); *A61K 38/191* (2013.01); *A61K 39/3955* (2013.01); *A61K 2039/505* (2013.01); *C07K 14/525* (2013.01); *C07K 14/705* (2013.01); *C07K 14/7151* (2013.01); *C07K 16/28* (2013.01); *C07K 16/2863* (2013.01); *C07K 2316/95* (2013.01); *C07K 2317/75* (2013.01)

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,376,110 A | 3/1983 | David et al. |
| 4,518,584 A | 5/1985 | Mark et al. |
| 4,575,013 A | 3/1986 | Bartley |
| 4,654,307 A | 3/1987 | Morgan |
| 4,719,179 A | 1/1988 | Barany |
| 4,737,462 A | 4/1988 | Mark et al. |
| 4,745,051 A | 5/1988 | Smith et al. |
| 4,761,367 A | 8/1988 | Edgell et al. |
| 4,870,009 A | 9/1989 | Evans et al. |
| 4,952,496 A | 8/1990 | Studier et al. |
| 5,093,246 A | 3/1992 | Cech et al. |
| 5,109,124 A | 4/1992 | Ramachandran et al. |
| 5,118,627 A | 6/1992 | Browne |
| 5,122,463 A | 6/1992 | Varshavsky et al. |
| 5,168,062 A | 12/1992 | Stinski |
| 5,169,784 A | 12/1992 | Summers et al. |
| 5,173,403 A | 12/1992 | Tang et al. |
| 5,175,269 A | 12/1992 | Stavrianopoulos |
| 5,176,996 A | 1/1993 | Hogan et al. |
| 5,187,153 A | 2/1993 | Cordell et al. |
| 5,198,343 A | 3/1993 | DeGryse |
| 5,204,254 A | 4/1993 | Schmid et al. |
| 5,212,058 A | 5/1993 | Baker et al. |
| 5,212,286 A | 5/1993 | Lewicki et al. |
| 5,215,907 A | 6/1993 | Tang et al. |
| 5,218,088 A | 6/1993 | Gorenstein et al. |
| 5,220,013 A | 6/1993 | Ponte et al. |
| 5,223,483 A | 6/1993 | Thomas et al. |
| 5,229,279 A | 7/1993 | Peoples et al. |
| 5,242,687 A | 9/1993 | Tykocinski et al. |
| 5,243,041 A | 9/1993 | Fernandez-Pol |
| 5,244,805 A | 9/1993 | Miller |
| 5,256,775 A | 10/1993 | Froehler |
| 5,264,564 A | 11/1993 | Matteucci |
| 5,266,317 A | 11/1993 | Tomalski et al. |
| 5,278,050 A | 1/1994 | Summers |
| 5,362,718 A | 11/1994 | Skotnicki et al. |

(Continued)

FOREIGN PATENT DOCUMENTS

| | | |
|---|---|---|
| CA | 2451138 | 1/2003 |
| CN | 101253199 | 8/2008 |
| EP | 1405645 | 4/2004 |
| EP | 1246925 | 5/2008 |
| JP | 2009-505678 | 2/2009 |
| WO | WO89/07142 | 8/1989 |
| WO | WO91/13160 | 9/1991 |
| WO | WO93/01286 | 1/1993 |
| WO | WO94/09010 | 4/1994 |
| WO | WO95/16691 | 6/1995 |

(Continued)

OTHER PUBLICATIONS

Allan et al. CD4+ T-regulatory cells: toward therapy for human diseases. Immunol Rev 223: 391-421, 2008.*
Benghiat et al. Critical influence of natural regulatory CD25+ T cells on the fate of allografts in the absence of immunosuppression. Transplantation 79(6): 648-654, 2005.*
Meloni et al. Regulatory CD4+CD25+ T cells in the peripheral blood of lung transplant recipients: correlation with transplant outcome. Transplantation 77(5): 762-766, 2004.*

(Continued)

*Primary Examiner* — Bridget E Bunner
(74) *Attorney, Agent, or Firm* — Fish & Richardson P.C.

(57) ABSTRACT

Compositions specific for TNF-receptor superfamily member 25 (TNFRSF25, DR3) modulate the immune response by regulating T regulatory cells.

15 Claims, 15 Drawing Sheets

(56) References Cited

U.S. PATENT DOCUMENTS

| | | | |
|---|---|---|---|
| 5,434,065 | A | 7/1995 | Mahan et al. |
| 5,510,099 | A | 4/1996 | Short et al. |
| 5,567,440 | A | 10/1996 | Hubbell |
| 5,656,481 | A | 8/1997 | Baetge et al. |
| 5,693,622 | A | 12/1997 | Wolff et al. |
| 5,700,657 | A | 12/1997 | Beaudry et al. |
| 5,714,323 | A | 2/1998 | Ohshima et al. |
| 5,773,246 | A | 6/1998 | Keene et al. |
| 5,859,208 | A | 1/1999 | Fiddes et al. |
| 5,955,056 | A | 9/1999 | Short et al. |
| 5,985,644 | A | 11/1999 | Roseman et al. |
| 6,254,874 | B1 | 7/2001 | Mekalanos et al. |
| 6,534,061 | B1 | 3/2003 | Goddard |
| 6,713,061 | B1 | 3/2004 | Yu et al. |
| 7,226,617 | B2 | 6/2007 | Ding et al. |
| 7,300,774 | B1 | 11/2007 | Kornbluth |
| 7,357,927 | B2 * | 4/2008 | Yu et al. ............. 424/130.1 |
| 7,385,032 | B2 | 6/2008 | Tschopp |
| 7,723,454 | B2 | 5/2010 | Keller et al. |
| 7,736,657 | B2 | 6/2010 | Gaide et al. |
| 2002/0009773 | A1 | 1/2002 | Yu |
| 2002/0015703 | A1 | 2/2002 | Rennert |
| 2002/0111325 | A1 | 8/2002 | Li et al. |
| 2002/0150534 | A1 | 10/2002 | Yu |
| 2003/0092044 | A1 | 5/2003 | Goddard |
| 2003/0129189 | A1 | 7/2003 | Yu |
| 2003/0170203 | A1 | 9/2003 | Yu |
| 2004/0013655 | A1 | 1/2004 | Shiozawa |
| 2004/0156847 | A1 | 8/2004 | Miura |
| 2005/0123536 | A1 | 6/2005 | Law |
| 2005/0158831 | A1 | 7/2005 | Kornbluth |
| 2005/0282223 | A1 | 12/2005 | Tittle |
| 2006/0233751 | A1 * | 10/2006 | Bluestone et al. ............. 424/85.2 |
| 2007/0128184 | A1 | 6/2007 | Podack |
| 2008/0003221 | A1 | 1/2008 | Podack |
| 2008/0233119 | A2 | 9/2008 | Podack |
| 2009/0317388 | A1 | 12/2009 | Burkly et al. |
| 2011/0243951 | A1 | 10/2011 | Podack et al. |
| 2012/0029472 | A1 | 2/2012 | Podack et al. |
| 2012/0263718 | A1 | 10/2012 | Siegel et al. |
| 2012/0321645 | A1 * | 12/2012 | Podack et al. ............. 424/173.1 |
| 2012/0328559 | A1 | 12/2012 | Podack |
| 2013/0142793 | A1 | 6/2013 | Ledbetter et al. |
| 2014/0193410 | A1 | 7/2014 | Podack et al. |
| 2014/0286897 | A1 | 9/2014 | Podack |
| 2016/0015779 | A1 | 1/2016 | Podack |

FOREIGN PATENT DOCUMENTS

| | | |
|---|---|---|
| WO | WO95/30762 | 11/1995 |
| WO | WO96/01899 | 1/1996 |
| WO | WO96/39154 | 12/1996 |
| WO | WO96/41807 | 12/1996 |
| WO | WO97/03211 | 1/1997 |
| WO | WO98/02441 | 1/1998 |
| WO | WO99/15530 | 4/1999 |
| WO | 9923105 | 5/1999 |
| WO | 9943839 | 9/1999 |
| WO | 0064465 | 11/2000 |
| WO | WO01/14387 | 3/2001 |
| WO | 0135995 | 5/2001 |
| WO | WO01/85207 | 11/2001 |
| WO | 0211767 | 2/2002 |
| WO | 02094192 | 11/2002 |
| WO | WO02/100345 | 12/2002 |
| WO | 03000286 | 1/2003 |
| WO | 03039491 | 5/2003 |
| WO | 03043583 | 5/2003 |
| WO | WO03/068977 | 8/2003 |
| WO | 2005018571 | 3/2005 |
| WO | WO2006/127900 | 11/2006 |
| WO | 2007027751 | 3/2007 |
| WO | WO2007/041317 | 4/2007 |
| WO | 2011017303 | 2/2011 |
| WO | WO2012/170072 | 12/2012 |

OTHER PUBLICATIONS

Meloni et al. Peripheral CD4+CD25+ Treg cell expansion in lung transplant recipients is not affected by calcineurin inhibitors. Int Immunopharmacol 6: 2002-2010, 2006.*

"TNFRSF25" entry in the National Library of Medicine, www.nlm.nih.gov/cgi/mesh/2013/MB_cgi?mode=&index=23859&field=all&HM=&II=&PA=&form=&input=; downloaded May 3, 2013, three pages.*

Wolf et al. Tregs expanded in vivo by TNFRSF25 agonists promote cardiac allograft survival. Transplantation 94: 569-574, 2012.*

Chew et al. A novel secreted splice variant of vascular endothelial cell growth inhibitor. FASEB J 16(7): 742-744, published online Mar. 26, 2002; 27 pages.*

Neuhaus et al. mTOR inhibitors: an overview. Liver Transplant 7(6): 473-484, 2001.*

Bull, M. J. et al: "The death receptor 3-TNF-like protein 1A pathway drives adverse bone pathology in inflammatory arthritis," J. Exp. Med., vol. 205, No. 11:2457-2464; 2008.

Al-Lamki, Rafia S. et al.: "TL1A both promotes and protects from renal inflammation and injury," J Am Soc Nephrol, 2008, vol. 19:953-960.

Jin, S. et al.: "TL1A/TNFSF15 directly induces proinflammatory cytokines, including TNFalpha, from CD3+CD161+T cells to exacerbate gut inflammation," Society for Mucosal Immunology, 2012, pp. 1:14.

Zhang, Jun et al.: "Role of TL1A in the pathogenesis of rheumatoid arthritis," The Journal of Immunology, 2009, vol. 183:5350-5357.

Pappu, Bhanu P. et al.: "TL1A-DR3 interaction regulates Th17 cell function and Th17-mediated autoimmune disease," J. Exp. Med, 2008, vol. 205, No. 5:1049-1062.

Deyev, V. et al: "TNFR25 Expression on CD4(+) CD25(+) T Cells: Down Modulation of Regulatory Activity," Blood, 2006, vol. 108, No. 11:903A.

Akbari, O., et al: "Essential role of NKT cells producing IL-4 and IL-13 in the development of allergen-induced airway hyperreactivity," Nature Medicine, May 2003, vol. 9, No. 5:582-588.

Bamias, G. et al: "Expression, localization, and functional activity of TL1A, a novely TH1-polarizing cytokine in inflammatory bowel disease," The Journal of Immunology, 2003, vol. 171:4868-4874.

Bodmer, J.-L. et al: "TRAMP, a novel apoptosis-mediating receptor with sequence homology to tumor necrosis factor receptor 1 and Fas(Apo-1/CD95)," Immunity, 1997, vol. 6:79-88.

Branch, Andrea D.: "A good antisense molecule is hard to find," TIBS, Feb. 1998, vol. 23:45-50.

Chen, S.: "TGF-Beta1 Regulation of chemokine receptors in rat microglia and human macrophages," Journal of Interferon & Cytokine Research, 2005, vol. 25:650-659.

Chinnaiyan, AM et al: "Signal transduction by DR3, a death domain-containing receptor related to TNFR-1 and CD95," Science, Nov. 1996, vol. 274:990-992.

Cui, J. et al: "Requirement for V_alpha14 NKT cells in IL-12-Mediated rejection of tumors," Science, Nov. 1997, vol. 278:1623-1626.

Delprete, G. et al: "CD30-mediated signaling promotes the development of human T helper type 2-like T cells," J. Exp. Med., Dec. 1995, vol. 182:1655-1661.

Fang, Lei: "Death receptor 3 (TNFR-SF25) delivers a late-acting costimulatory signal for TH2 cytokine production during the development of allergic asthma," Dissertaton submitted to the faculty of the University of Miami, Coral Gables, Florida, 2004:1-153.

Gruenig, G. et al: "Requirement for IL-13 independently of IL-4 in experimental asthma," Science, Dec. 1998, vol. 282:2261-2263.

Harlin, H. et al: "TCR-independent CD30 signaling selectively induces IL-13 production via a TNF receptor-associated factor/p38 mitogen-activated protein kinase-dependent mechanism," The Journal of Immunology, 2002, pp. 2451-2460.

Huang, Z.: "Structural chemistry and therapeutic intervention of protein—protein interactions in immune response, human immunodeficiency virus entry, and apoptosis," Pharmacology & Therapeutics, 2000, vol. 86:201-215.

(56) References Cited

OTHER PUBLICATIONS

Kitson, J. et al:"A death-domain-containing receptor that mediates apoptosis," Nature, Nov. 1996, vol. 384:372-375.
Leonard, C. et al: "Allergen-induced CD30 expression on T cells of atopic asthmatics," Clinical and Experimental Allergy, 1997, vol. 27:780-786.
Li, L. et al: "Effects of Th2 cytokines on chemokine expression in the lung: IL-13 potently induces eotaxin expression by airway epithelial cells," The Journal of Immunology, 1999, vol. 162:2477-2487.
Marsters, S. A.: "Apo-3, a new member of the tumor necrosis factor receptor family, contains a death domain and activates apoptosis and NF-kB," Current Biology, 1996, vol. 6:1669-1676.
Mattes, J. et al: "IL-13 induces airways hyperreactivity independently of the IL-4R alpha chain in the allergic lung," The Journal of Immunology, 2001, vol. 167:1683-1692.
Migone, T.S. et al: "TL1A is a TNF-like ligand for DR3 and TR6/DcR3 and functions as a T cell costimulator," Immunity, Mar. 2002, vol. 16:479-492.
Nam, S.-Y. et al: "CD30 deficiency diminishes airway eosinophillia in a mouse model of pulmonary inflammation," FASEB Journal, May 6-10, 2003, Denver, Colorado, Abstract 30.24.
Prehn, J.L. et al: "Potential role for TL1A, the new TNF-family member and potent costimulator of IFN-gamma, in mucosal inflammation," Clin Immunol., Jul. 2004, vol. 112:66-77.
Wen, L. et al: "TL1A-induced NF-kB activation and c-IAP2 production prevent DR-3 mediated apoptosis in TF-1 cells," The Journal of Biological Chemistry, Oct. 2003, vol. 278:39251-39258.
Purello-D'Ambrosio, F. et al: "Effect of fluticasone propionate on soluble CD30 release in patients with severe allergic asthma," Invest Allergol lin Immunol, Sep.-Oct. 2000, vol. 10:283-285.
Screaton, G.R. et al: "LARD: A new lymphoid-specific death domain containing receptor regulated by alternative pre-mRNA splicing," Proc. Natl. Acad. Sci, Apr. 1997, vol. 94:4615-4619.
Tan, K.B. et al: "Characterization of a novel TNF-like ligand and recently described TNF ligand and TNF receptor superfamily genes and their constitutive and inducible expression in hematopoietic and non-hematopoietic cells," Gene, Dec. 1997, vol. 204:35-46.
Wang, E.C.Y. et al: "DR3 regulates negative selection during thymocyte development," May 2001, Molecular and Cellular Biology, vol. 21:3451-3461.
Wills-Karp, M. et al: "Interleukin-13: Central mediator of allergic asthma," Science, Dec. 1998, vol. 282:2258-2260.
Wen, T. et al: "4-1BB Ligand-mediated costimulation of Human T Cells induces CD4 and CD8 T cell expansion, cytokine production, and the development of cytolytic effector function," The Journal of Immunology, 2002, vol. 168:4897-4906.
Shuford, W.W. et al: "4-1BB costimulatory signals preferentially induce CD8+ T cell proliferation and lead to the amplication in vivo of cytotoxic T cell responses," J. Exp. Med., 1997, vol. 186:47-55.
Miller, R.E. et al: "4-1BB-specific monoclonal antibody promotes the generation of tumor-specific immune responses by direct activation of CD8 T cells in a CD40-dependent manner, " The Journal of Immunology, 2002, vol. 169:1792-1800.
Papadakis, K.A. et al: "TL1A synergizes with IL-12 and IL-18 to enhance IFN-gamma production in human T cells and NK cells," The Journal of Immunology, 2004, vol. 172:7002-7007.

Sanchez-Fueyo, A. et al.: "CD4+CD25+ regulatory T cells in transplantation tolerance," Immunologia, 2004, vol. 23, No. 2:231-238.
Pulendran, "Modulating vaccine responses with dendritic cells and Toll-like receptors," Immunol Rev., 199:227-250, Jun. 2004.
Watts, "TNF/TNFR family members in costimulation of T cell responses," Annu Rev Immunol., 23:23-68, 2005.
Al-Lamki et al., "Expression of silencer of death domains and death-receptor-3 in normal human kidney and in rejecting renal transplants," *Am J Pathol.*, 163(2):401-411, Aug. 2003.
Berg et al., "ACRP30/adiponectin: an adipokine regulating glucose and lipid metabolism," *Trends Endocrinol Metab.*, 13(2):84-89, Mar. 2002.
Chinnaiyan et al., "Signal transduction by DR3, a death domain-containing receptor related to TNFR-1 and CD95," *Science.*, 274(5289):990-992, Nov. 8, 1996.
Cobrin and Abreu, "Defects in mucosal immunity leading to Crohn's disease," *Immunol Rev.*, 206:277-295, Aug. 2005.
Khan et al., "Cloning, expression, and functional characterization of TL1A-Ig;" *J Immunol.*, 190(4):1540-1550, Epub Jan. 14, 2013.
Kitson et al., "A death-domain-containing receptor that mediates apoptosis," *Nature*, 384(6607):372-375, Nov. 28, 1996.
Papadakis et al., "Dominant role for TL1A/DR3 pathway in IL-12 plus IL-18-induced IFN-gamma production by peripheral blood and mucosal CCR9+ T lymphocytes," *J Immunol.*, 174(8):4985-4990, Apr. 15, 2005.
R&D Systems, "Adiponectin/Acrp30: Products," R&D Systems [online], as appeared on Jan. 26, 2013 [retrieved on Sep. 9, 2014]. Retrieved from the Internet: < URL:http://web.archive.org/web/20130126225534/http://rndsystems.com/product_results.aspx?m=1034>, 2 pages.
Schreiber et al. "T cell costimulation by TNFR superfamily (TNFRSF)4 and TNFRS25 in the context of vaccination," *J Immunol.*, 189(7):3311-3318, Epub Sep. 5, 2012.
Schreiber et al., "Therapeutic Treg expansion in mice by TNFRSF25 prevents allergic lung inflammation," *J Clinc Invest.*, 120(10):3629-36240, Oct. 2010.
Takedatsu et al., "TL1A (TNFSF15) regulates the development of chronic colitis by modulating both T-helper 1 and T-helper 17 activation," *Gastroenterology*, 135(2):552-567, Epub May 7, 2008.
Tan et al., "Characterization of a novel TNF-like ligand and recently described TNF ligand and TNF receptor superfamily genes and their constitutive and inducible expression in hematopoietic and non-hematopoietic cells," *Gene*, 204(1-2):35-46, Dec. 19, 1997.
European Search Report and Written Opinion in App. No. EP 10807012.9 dated Mar. 5, 2013, 7 pages.
International Preliminary Report on Patentability for PCT/US2010/44218, completed Dec. 3, 2011, 8 pages.
International Search Report for PCT/US2010/44218, mailed Sep. 27, 2010, 1 page.
Reddy, "TNFRSF25 agonistic antibody and galectin-9 combination therapy controls herpes simplex virus-induced immunoinflammatory lesions," J Virol., 86(19):10606-10620, Epub Jul. 18, 2012.
Schreiber et al., "The role of TNFRSF25:TNFSF15 in disease . . . and health?" Adv Exp Med Biol., 691:289-298, 2011.
Kim et al., "Treatment with agonistic DR3 antibody results in expansion of donor Tregs and reduced graft-versus-host disease," Blood., 126(4):546-557, Epub Jun. 10, 2015.

\* cited by examiner

METHOD FOR IN VIVO EXPANSION OF T REGULATORY CELLS

CROSS REFERENCE TO RELATED APPLICATIONS

This application claims priority to U.S. provisional application No. 61/273,299, filed Aug. 3, 2009, which is incorporated herein by reference in its entirety.

STATEMENT REGARDING FEDERALLY SPONSORED RESEARCH

This application is the U.S. national phase under 35 U.S.C. 371 of international application number PCT/US10/044218, filed Aug. 3, 2010, which designated the U.S. and claims priority to U.S. provisional application No. 61/273,299, filed Aug. 3, 2009, which are incorporated herein by reference in their entirety.

FIELD OF THE INVENTION

Embodiments of the invention relate to compositions and methods for regulating T cells in vivo. In particular, the compositions and methods regulate human $CD4^+FoxP3^+$ cells.

BACKGROUND

The tumor necrosis factor superfamily (TNFSF) consists of at least 19 ligands and 30 receptors (TNFRSF) that are differentially and temporally expressed by both lymphoid and non-lymphoid lymphoid cells. In $CD3^+$ T cells, TNFSF signals function in both antigen specific and non-specific ways to support various phases of an immune response including polarization, expansion, effector function, contraction, memory and death. TNFSF15 (TL1A) is the ligand for TNFRSF25 (DR3, hereafter referred to as TNFR25) and can modulate TNFR25-expressing T and NKT cells either positively or negatively by triggering TRADD or FADD signaling cascades via the death domain-containing cytoplasmic tail of TNFR25. TNFR25 signaling is an important contributor to the pathology observed in a range of autoinflammatory conditions including asthma, inflammatory bowel disease (IBD), experimental autoimmune encephalomyelitis (EAE) and rheumatoid arthritis (RA). Antibody blockade of TL can prevent acute asthma in mice and genetic knockout of TNFR25 significantly blunts the pathologic events in experimental models of EAE or RA. TL contributes to the development of these disease by enhancing polarization, differentiation and effector function of NKT, Th2 and Th17 cells.

SUMMARY

This Summary is provided to present a summary of the invention to briefly indicate the nature and substance of the invention. It is submitted with the understanding that it will not be used to interpret or limit the scope or meaning of the claims.

Signaling through the TNF-receptor superfamily member 25 (TNFRSF25, DR3) on $CD4^+$ T cells, where it is constitutively expressed, enhances $T_H2$ and $T_H17$ cytokine production and contributes to pathological inflammation in disease models of asthma, inflammatory bowel disease, multiple sclerosis (MS), experimental autoimmune encephalitis and rheumatoid arthritis.

In preferred embodiments, agents which modulate TNFRSF25 signaling modulate immune cell response. These agents provide novel therapies for diseases and conditions thereof. For example, an agonist of TNFRSF25 led to the rapid and extensive in vivo expansion of $CD4^+FoxP3^+$ cells to 30-35% of all $CD4^+$ cells within four days of administration. The rise in $CD4^+FoxP3^+$ cells was due to increased proliferation of $CD4^+FoxP3^+CD25^+$ cells expressing high levels of GITR and CD103. TNFRSF25 agonist expanded $CD4^+FoxP3^+$ cells retained TGF-β-dependent suppressive activity ex vivo, which however was susceptible to abrogation by continued TNFRSF25 signaling. TNFRSF25 signaling in addition to modulating effector cell responses plays an important role in both the induction and resolution of inflammatory responses via control of T regulatory cell expansion and activity.

Other aspects of the invention are described infra.

BRIEF DESCRIPTION OF THE DRAWINGS

FIG. 1A: Differential expression of TNFR25, GITR, OX40 and 4-1BB on conventional and regulatory T cells. TNFRSF expression was determined by flow cytometry on highly purified $CD4^+FoxP3^-$ (Tconv) and $CD4^+FoxP3^+$ Treg from splenocytes harvested from untreated FIR mice. FIG. 1B: Kinetics and dose-dependent expansion of $CD4^+FoxP3^+$ Treg cells in peripheral blood after 4C12 injection. FoxP3-RFP reporter (FIR) mice were injected intraperitoneally (i.p.) with the amount of purified 4C12 indicated. The mice were bled daily and FoxP3-RFP expression analyzed in peripheral blood cells by flow cytometry. FIG. 1C: Treg expansion was compared following treatment with other TNFR agonistic antibodies. Mice were injected i.p. with the indicated antibodies (100 μg) on day 0. Mice were bled daily as in FIG. 1B for 6 days, the percentage of peripheral blood Treg out of total $CD4^+$ T cells on day 4 is shown. These data have been reproduced in over 8 independent experiments. Error bars indicate mean±SEM. Significance was determined by the student's t-test (FIG. 1B) or one-way ANOVA with Tukey post test (FIG. 1C). * indicates p<0.05,  indicates p<0.01, * indicates p<0.001.

FIG. 3A: CD4+ FoxP3+ cells were purified from FIR mice on day 4 after treatment with control IgG or 4C12 antibodies and incubated with the indicated amounts of IL-2 in vitro. $CD4^+FoxP3^+$ cell proliferation was measured on day 3 of the culture by incorporation of tritiated thymidine. FIG. 3B: $CD4^+FoxP3^+$ cells were purified as in (FIG. 3A) and the surface expression of IL-2Rγ (CD132) or IL-2Rβ (CD122) was determined by flow cytometry. FIG. 3C: $CD4^+FoxP3^+$ cells purified from FIR mice 4 days after treatment with IgG or 4C12 antibody were analyzed for expression of pSTAT5 15 minutes after treatment with 10 ng/ml of IL-2 in vitro. FIR mice were treated once daily with rapamycin (FIG. 3D) or twice daily with Akt inhibitor V (FIG. 3E) or a vehicle control from day-1 through day-4 by i.p. injection as described in the methods. Mice were treated with either 4C12 or control IgG antibody on day 0 and the proportion of FoxP3-RFP positive cells relative to total $CD4^+$ cells in the peripheral blood was analyzed on day-4. These data are represented as the mean±S.E.M. of at least 2 independent experiments with ≥2 mice per group per experiment. ns indicates not significant, *** indicates p<0.001.

FIG. 4A: Peripheral blood was collected and analyzed for the fraction of CD4+FoxP3+ cells out of total CD4+T cells from ova/alum immunized mice as compared to non-immunized mice following treatment with either 4C12 or isotype control antibody. Data indicate mean±SEM. FIG. 4B: Total lung cells were harvested and analyzed by flow cytometry. The total number of each indicated cell population are shown. Data indicate mean±SEM. FIG. 4C: The percentage of CD4+FoxP3+ Treg out of total CD4+T cells. FIG. 4D: Bronchio alveolar lavage fluid (BALF) was collected 3 days after aerosolization with ova/PBS as described. The total number of eosinophils is shown. Data indicate mean±SEM. FIG. 4E: Total RNA was extracted from total lung cells and used for real-time RT-PCR. The expression levels of IL-4, IL-5 and IL-13 in 4C12 or isotype control treated mice are shown relative to saline-aerosolized control lung cells. FIG. 4F: Lungs were harvested and sectioned for histological sections. H&E (left panels) as well as PAS (right panels) were obtained for each treatment group. Representative images are shown. These data have been repeated in four independent experiments with at least 3 mice/group/experiment. FIG. 4G: PAS stained sections were quantitated using Image J software as described in the methods. Two representative images were quantitated from each of ≥5 mice from 2 separate experiments. Statistical significance was determined by one-way ANOVA with Tukey's post-test. * indicates p<0.05,  indicates p<0.01, * indicates p<0.001 of either 4C12 or 1AC as compared to the IgG group or saline-control group, as indicated.

FIG. 5A: FIR mice were treated with IgG or 4C12 on day 0 and splenocytes were harvested 4 days later and analyzed by flow cytometry. Representative flow cytometry plots from peripheral blood cells collected from mice 4 days after the indicated treatment. FIG. 5B: The average ratio of CD25hi versus CD25int Treg in splenocytes 4 days after the indicated treatment. FIG. 5C: Representative dot plots are shown that were pre-gated on CD4+, FoxP3+ cells. Percentages indicate the contribution of each phenotype toward the total fraction of CD4+FoxP3+ cells. FIG. 5D: The average proportion of Ki67+or Ki67- among CD25hi and CD25int Treg following the indicated treatment as described in FIG. 5A is shown. Data are mean±SEM. FIG. 5E: CD4+FoxP3 and FIG. 5F: CD4+FoxP3+ cells were sorted from CD45.2+FIR mice to >99% purity and 2×106 cells from each subset were adoptively transferred into CD45.1 congenic B6-SJL mice. 24 h later, mice were injected i.p. with 20 mg 4C12 or IgG, respectively. FIGS. 5E, 12G: Transfer of CD4+FoxP3- and (FIGS. 5F, 5H) CD4+FoxP3+ cells into congenic CD45.1 B6-SJL mice. FIGS. 5E, 5F: Histogram showing the percentage of CD45.2+ and RFP (FoxP3+) cells among CD4+ cells on day 5 after adoptive transfer. FIGS. 5G, 5H: Kinetics of transferred cell contraction following 4C12 or hamster IgG treatment. The percentage of transferred cells (CD45.2+CD4+) out of host CD45.1+CD4 +FoxP3- cells (FIG. 5E) or CD45.24CD4+FoxP3 out of host CD45.1+ CD4+ cells (FIG. 5F) are shown. Error bars indicate average percentage±SEM for 3 mice per group for each of two independent experiments. * indicates p<0.05 and ** indicates p<0.01.

In FIGS. 6C and 6D, IgG, 4C12 or DTA1 (10 g/ml) antibodies were added to the suppression assay. The Treg:Teff ratio was kept constant at a 1:2 ratio. FIG. 6E: Teff cells from TNFR25 dominant negative (DN) mice and Treg cells from wt mice were used. IgG or 4C12 antibodies (10 μg/ml) were added to the suppression assay. The Treg:Teff ratio is 1:2. FIG. 6F: $CD4^+CD25^{hi}$ and $CD4^+CD25^{int}$ Treg cells from IgG or 4C12 injected mice were used. $^3$H-thymidine was added for the last 6 h before the assay was analyzed on a scintillation counter. Percent proliferation was calculated using the counts obtained for the indicated condition as a percentage of the total counts obtained in wells containing Teff in the absence of Tregs. Data are expressed as the average±SEM with ≥4 samples for each condition in each of two independent experiments with >6 mice per group per experiment.

FIG. 7A: FIR mice were treated with 4C12 (10 μg) on day 0 or with a series of three injections with IAC on days 0-2. The proportion of $FoxP3^+$ cells within the CD4+ T cell population was measured in the peripheral blood daily by flow cytometry. FIG. 7B: Splenocytes were isolated from FIR mice 4 on day 4 after treatment with IAC, 4C12 or isotype control IgG. The proportion of $CD4^+FoxP3^+$ cells expressing CD25 and the proliferation marker Ki67 are shown.

FIG. 8A: An example of a typical flow cytometry dot plot staining for CD4 and FoxP3 (RFP). $CD4^+FoxP3^+$ cells from quadrant Q2-1 were gated for subsequent analysis of $CD25^{hi}$ and $CD25^{int}$ cells as shown in FIGS. 8B-8D. FIG. 8B: The ratio of GITR and FIG. 8C: CD103 expression among $CD25^{hi}$ versus $CD25^{int}$ Treg in splenocytes 4 days after the indicated treatment. FIG. 8D: Data are represented as mean±SEM from over 8 independent experiments with at least 3 mice per group per experiment. Paired analysis was performed using the students T-test.  indicates p<0.01 and * indicates p<0.001.

FIG. 9A: Splenocytes were harvested from FIR mice, enriched for CD4+ T cells and sorted on the basis of CD4+ and FoxP3+ (RFP). The left panel illustrates a typical CD4-enriched population of splenocytes. The middle and right panels illustrate representative post-sort analysis for CD4+FoxP3− (P3 gate) and CD4+FoxP3+ (P4 gate) populations. FIG. 9B: For some experiments CD4+FoxP3+ cells (gate P3) were sorted based on CD25 expression. Representative plots are shown demonstrating the gating strategy for CD25$^{hi}$ and CD25$^{int}$ sorting.

DETAILED DESCRIPTION

Figures 1A, 1B, 1C:
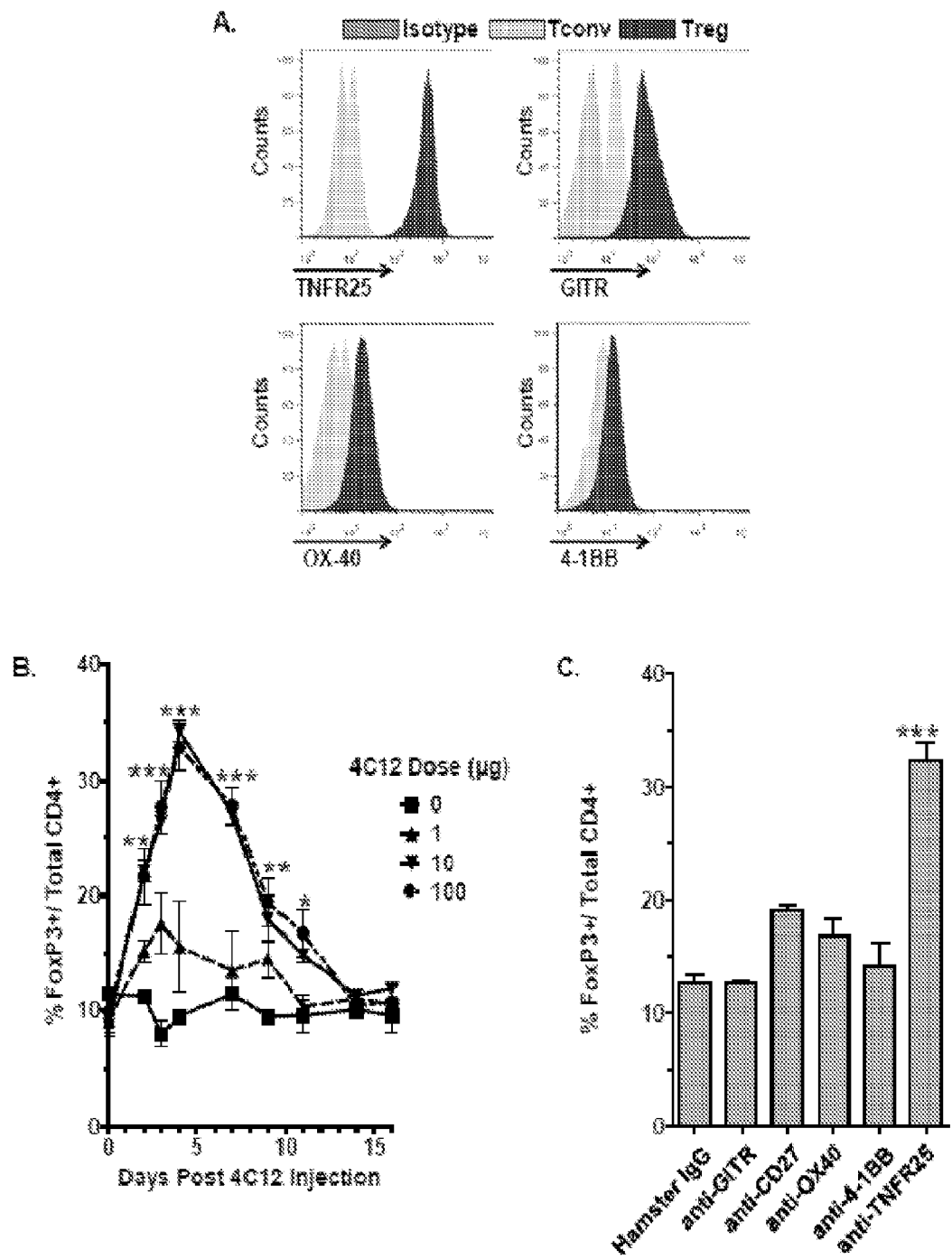
FIGS. 1A-1C: show that TNFR25 stimulates the rapid proliferation of CD4+ FoxP3+ cells in vivo.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the molecules disclosed herein e.g. 4C2 is not limited to mice but the human antibody is preferred, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

A "T regulatory cell" or "Treg cell" or "Tr cell" refers to a cell that can modulate a T cell response. Treg cells express the transcription factor Foxp3, which is not upregulated upon T cell activation and discriminates Tregs from activated effector cells. Tregs are identified by the cell surface markers CD25, CTLA4, and GITR. Several Treg subsets have been identified that have the ability to inhibit autoimmune and chronic inflammatory responses and to maintain immune tolerance in tumor-bearing hosts. These subsets include interleukin 10- (IL-10-) secreting T regulatory type 1 (Tr1) cells, transforming growth factor-β- (TGF-β-) secreting T helper type 3 (Th3) cells, and "natural" $CD4^+/CD25^+$ Tregs (Trn) (Fehervari and Sakaguchi. *J. Clin. Invest.* 2004, 114:1209-1217; Chen et al. *Science.* 1994, 265: 1237-1240; Groux et al. *Nature.* 1997, 389: 737-742).

"TNFR25 agonist", "TNFR25 agent", "TNFR25 composition" are used interchangeably herein and refer to a substance that binds to the TNFR25 receptor and triggers a response in the cell on which the TNFR25 receptor is expressed similar to a response that would be observed by exposing the cell to a natural TNFR25 ligand, e.g., TL1A. An agonist is the opposite of an antagonist in the sense that while an antagonist may also bind to the receptor, it fails to activate the receptor and actually completely or partially blocks it from activation by endogenous or exogenous agonists. A partial agonist activates a receptor but does not cause as much of a physiological change as does a full agonist. Alternatively, another example of a TNFR25 agonist is an antibody that is capable of binding and activating TNFR25. An example of an anti-TNFR antibody is 4C12 (agonist). (Deposited under the Budapest Treaty on Behalf of: University of Miami; Date of Receipt of seeds/strain(s) by the ATCC®: May 5, 2009; ATCC® Patent Deposit Designation: PTA-10000. Identification Reference by Depositor: Hybridoma cell line; 4C12; The deposit was tested Jun. 4, 2009 and on that date, the seeds/strain(s) were viable. International Depository Authority: American Type Culture Collection (ATCC®), Manassas, Va., USA).

"TNFR25 antagonist" is referred to herein as a substance that inhibits the normal physiological function of a TNFR25 receptor. Such agents work by interfering in the binding of endogenous receptor agonists/ligands such as TL1A, with TNFR25 receptor.

TNFR25 antagonists or agonists may be in the form of aptamers. "Aptamers" are DNA or RNA molecules that have been selected from random pools based on their ability to bind other molecules. The aptamer binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chem.* 45:1628, 1999).

As used herein, the term "antibody" is inclusive of all species, including human and humanized antibodies and the antigenic target, for example, TNFR25, can be from any species. Thus, an antibody, for example, anti-TNFR25 can be mouse anti-human TNFR25, goat anti-human TNFR25; goat anti-mouse TNFR25; rat anti-human TNFR25; mouse anti-rat TNFR25 and the like. The combinations of antibody generated in a certain species against an antigen target, e.g. TNFR25, from another species, or in some instances the same species (for example, in autoimmune or inflammatory response) are limitless and all species are embodied in this invention. The term antibody is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)$_2$, Fv, single chain antibodies, diabodies), comprising complementarity determining regions (CDRs) of the foregoing as long as they exhibit the desired biological activity.

"Target molecule" includes any macromolecule, including protein, carbohydrate, enzyme, polysaccharide, glycoprotein, receptor, antigen, antibody, growth factor; or it may be any small organic molecule including a hormone, substrate, metabolite, cofactor, inhibitor, drug, dye, nutrient, pesticide, peptide; or it may be an inorganic molecule including a metal, metal ion, metal oxide, and metal complex; it may also be an entire organism including a bacterium, virus, and single-cell eukaryote such as a protozoon.

"Treating" or "treatment" of a state, disorder or condition includes: (1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) Inhibiting the state, disorder or condition, i.e., arresting, reducing or delaying the development of the disease or a relapse thereof (in case of maintenance treatment) or at least one clinical or subclinical symptom thereof; or (3) Relieving the disease, i.e., causing regression of the state, disorder or condition or at least one of its clinical or sub-clinical symptoms. The benefit to a subject to be treated is either statistically significant or at least perceptible to the patient or to the physician.

"Patient" or "subject" refers to mammals and includes human and veterinary subjects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Immune Response Modulation

Characteristics of CD4 T cell subsets: CD4 T cells upon activation and expansion develop into different T helper ($T_H$) cell subsets with different cytokine profiles and distinct effector functions. Appropriate differentiation of $T_H$ cells into effector subsets best suited for host defense against an invading pathogen is of critical importance to the immune system. CD4 T cells differentiate into at least four known subsets, three effector subsets ($T_H1$, $T_H2$ and $T_H17$) and one T regulatory subset (Treg). Based on the cytokines that they produce, T cells were historically divided into $T_H1$ and $T_H2$ cells, and this has provided a framework to understand how specific cytokine milieus produced by cells of the innate immune system guide the development of adaptive immunity. $T_H1$ cells, which are potently induced by dendritic cells (DC) secreting IL-12, are characterized by the expression of the lineage-specific transcription factor T-bet (T box 21) and the production of IFN-$\gamma$. $T_H2$ cells, which depend on IL-4 during differentiation and lack of IL-12, produce IL-4, IL-5, IL-9, and IL-13 and are characterized by the expression of the transcription factor GATA-3. Importantly, in the past five years, a third subset of IL-17-producing effector T helper cells, called $T_H17$ cells, has been discovered and characterized and is specified by expression of the transcription factor ROR$\gamma$t.

$T_H17$ cells produce IL-17, IL-17F, and IL-22. By secreting these effector cytokines, $T_H17$ cells induce a massive tissue reaction due to the broad distribution of the IL-17 and IL-22 receptors. $T_H17$ cells also secrete IL-21 to communicate with the cells of the immune system. Synergy between the cytokines transforming growth factor beta isoform 1 (TGF-$\beta$) and interleukin (IL)-6 induces development of $T_H17$ cells in mice and humans, while IL-23 supports expansion of these cells. The differentiation factors (TGF-3 plus IL-6 or IL-21), the growth and stabilization factor (IL-23), and the transcription factors (STAT3, ROR-$\gamma$t (ROR-c), and ROR-a) involved in the development of $T_H17$ cells have only recently been identified. The participation of TGF-$\beta$ in the differentiation of $T_H17$ cells places the $T_H17$ lineage in close relationship with CD4$^+$CD25$^+$Foxp3$^+$ regulatory T cells ($T_{reg}$) since TGF-$\beta$ also induces differentiation of naive T cells into Foxp3$^+$ Treg in the peripheral immune compartment. Treg cells are a specialized subpopulation of T cells that act to suppress activation of the immune system and thereby maintain immune system homeostasis and tolerance to self-antigens. Development of Treg cells, which are capable of suppressing autoimmune disease, is reciprocally related to $T_H17$ cells, which can drive immune responses, including autoimmune responses. Treg cells can be identified by their unique expression of the transcription factor forkhead box P3 (Foxp3). Importantly, so far as is known, there are two phenotypically identical populations of CD4$^+$CD25$^+$ Treg—natural and adaptive. Natural CD4$^+$CD25$^+$ Treg cells arise in the thymus under homeostatic conditions to safeguard against autoimmunity. Adaptive CD4$^+$CD25$^+$ Treg cells arise during inflammatory processes such as infections and cancers and suppress immunity through heterogeneous mechanisms that include direct contact or the production of soluble factors such as IL-10 and TGF-$\beta$.

Tumor Necrosis Factor Receptor 25 (TNFR25): Interchangeably referred to herein as Death receptor 3 (DR3), is a regulator of T cell function. Death receptor 3 (DR3) (Chinnaiyan et al., *Science* 274:990, 1996) is a member of the TNF-receptor family. It is also known as TRAMP (Bodmer et al., *Immunity* 6:79, 1997), wsl-1 (Kitson et al., *Nature* 384:372, 1996), Apo-3 (Marsters et al., *Curr Biol* 6:1669, 1996), and LARD (Screaton et al., *Proc Natl Acad Sci USA* 94:4615, 1997) and contains a typical death domain. Transfection of 293 cells with human DR3 (hDR3) induced apoptosis and activated NF-KB. Multiple spliced forms of human DR3 mRNA have been observed, indicating regulation at the post transcriptional level (Screaton et al., *Proc Natl Acad Sci USA* 94:4615, 1997).

CD4$^+$FoxP3$^+$ regulatory T cells (Treg) can suppress the activity of autoreactive effector T cells that escape negative selection in the thymus. Tregs are sufficient to prevent or delay autoimmune pathology in experimental models of IBD, asthma and EAE. TNFR25 signaling blocks Tregs from inhibiting CD4$^+$CD25$^-$ but not antigen-specific CD8$^+$ cells in vitro. Interestingly, transgenic mice expressing full-length TNFR25 under the CD2 promoter express high levels of $T_H2$ and $T_H17$ cytokines and have decreased cellularity in secondary lymphoid tissues. The coincidence of decreased regulatory T cell activity, decreased cellularity and increased cytokine production in TNFR25 transgenic mice suggests that TNFR25 signaling may be both pro- and anti-inflammatory depending on the context in which TNFR25 signals are received.

Briefly, the experiments conducted herein, showed the unexpected finding that in vivo stimulation of TNFR25 leads to the rapid and systemic expansion of the CD4$^+$FoxP3$^+$ regulatory T cell pool. Antibody (4C12) induced Treg expansion occurred independently of exogenous antigen and resulted in a 3-4 fold increase in the percentage of Tregs out of total CD4$^+$ cells within 4 days of administration. This Treg expansion resulted predominantly from the proliferation of CD4$^+$FoxP3$^+$CD25$^{int}$ cells, is durable, and does not contract to unstimulated levels for two weeks. 4C12 expanded Tregs retain TGF mediated effector T cell suppressor functions ex vivo; however continued TNFR25-signaling abrogates the suppressive activity of 4C12 expanded Tregs. Without wishing to be bound by theory, these findings indicate that TNFR25 signaling in Tregs has the dual function of increasing Treg proliferation and inhibition of Treg suppressor activity. Inhibition of Treg suppression by TNFR25 signaling is highly plastic and can be restored or maintained following removal or continuation of TNFR25 signaling in Tregs, respectively. The addition of this information to the role of TNFR25 as a costimulator of $T_H2$ and $T_H17$ responses indicates that the role of TNFR25 in immune signaling is to simultaneously enhance effector cell function during the induction of an inflammatory response and accelerate resolution of inflammation via a regionally expanded pool of Tregs that regain suppressive activity following removal of the inflammatory stimulus. Taken together, these findings evidence that TNFR25 targeted therapies may be valuable to either enhance or inhibit immune activation, depending on the inflammatory context in which they are administered; with broad implications to the fields of autoimmune disease, chronic infection, transplantation and cancer.

In one preferred embodiment, a method of regulating an immune response in vivo comprises administering to a patient in need thereof, at least one agent which modulates tumor necrosis factor superfamily receptor 25 (TNFRSF25; TNFR25; DR3) function. The preferred function is TNFRSF25 mediated signaling which results in the induction of regulatory T cell (Treg) proliferation. Stimulation of the TNFRSF25 molecule induces Treg cells which suppress an immune response. However, continued stimulation of the TNFRSF25 molecule abrogates the suppressive activity of the Treg cells, thus, regulating an immune response.

Signaling through the TNF-receptor superfamily member 25 (TNFRSF25, DR3) on CD4$^+$ T cells, where it is constitutively expressed, enhances $T_H2$ and $T_H17$ cytokine production and contributes to pathological inflammation in disease models of asthma, inflammatory bowel disease, multiple sclerosis (MS), and rheumatoid arthritis.

In preferred embodiments regulating the immune response in vivo treats diseases or disorders associated with an immune response. Such diseases or disorders comprise, for example: rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.; graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; infections caused by pathogenic microorganisms (e.g. *Aspergillus fumigatus, Fusarium oxysporum, Trichophyton asteroides*, etc.); inflammatory or hyperproliferative skin diseases or cutaneous manifestations of immunologically mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata); autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.); reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.; mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases); intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migrain, rhinitis and eczema); renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's diseases Parkinson's diseases, amyotrophic lateral sclerosis (ALS) and radiculopathy); cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction); endocrine diseases (e.g. hyperthyroidism, and Basedow's disease); hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia); bone diseases (e.g. osteoporosis); respiratory diseases (e.g. sarcoidosis, pulmonary fibrosis, and idiopathic interstitial pneumonia); skin diseases (e.g. dermatomyositis, leukoderma vulgaris, ichthyosis vulgaris, photosensitivity, and cutaneous T-cell lymphoma); circulatory diseases (e.g. arteriosclerosis, atherosclerosis, aortitis syndrome, polyarteritis nodosa, and myocardosis); collagen diseases (e.g. scleroderma, Wegener's granuloma, and Sjogren's syndrome); adiposis; eosinophilic fasciitis; periodontal diseases (e.g. damage to gingiva, periodontium, alveolar bone or substantia ossea dentis); nephrotic syndrome (e.g. glomerulonephritis); male pattern alopecia, alopecia senile; muscular dystrophy; pyoderma and Sezary syndrome; chromosome abnormality-associated diseases (e.g. Down's syndrome); Addison's disease; active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)); intestinal diseases (e.g. endotoxin shock, pseudomembranous colitis, and drug- or radiation-induced colitis); renal diseases (e.g. ischemic acute renal insufficiency, chronic renal failure); pulmonary diseases (e.g. toxicosis caused by pulmonary oxygen or drugs (e.g. paracort, bleomycin, etc.), lung cancer, and pulmonary emphysema); ocular diseases (e.g. cataracta, iron-storage disease (siderosis bulbi), retinitis, pigmentosa, senile plaques, vitreous scarring, corneal alkali burn); dermatitis (e.g. erythema multiforme, linear immunoglobulin A bullous dermatitis, cement dermatitis); and other diseases (e.g. gingivitis, periodontitis, sepsis, pancreatitis, and diseases caused by environmental pollution (e.g. air pollution), aging, carcinogen, metastasis of carcinoma, and hypobaropathy)]; diseases caused by histamine release or leukotriene C4 release; restenosis of coronary artery following angioplasty and prevention of postsurgical adhesions; autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis); Human Immunodeficiency Virus (HIV) infection, AIDS; allergic conjunctivitis; hypertrophic cicatrix and keloid due to trauma, burn, or surgery.

In one preferred embodiment, the agent is administered in a single dose or spread out over a period of time in order to maintain the suppressive effects of Treg cells. For example, treatment of autoimmune diseases.

In another preferred embodiment, the agent is administered in multiple or a plurality of doses so that the suppressive effects of the Treg cells are abrogated. For example, in the treatment of cancer, viral diseases or other diseases requiring an immune mediated clearing of abnormal cells.

In another preferred embodiment, the agent is administered in an extended release formulation so as to provide a constant stimulation of TNFRSF25 so as to abrogate the suppression of the immune system by Treg cells.

In another preferred embodiment, at least one agent stimulates signaling of TNFRSF25 and induces proliferation of CD4+FoxP3+CD25$^{int}$ cells in a patient. The suppressive effects of the Treg cells can be monitored and the doses of the agent can be adjusted to maintain the suppressive effects in diseases or conditions wherein a decreased immune response is desired, for example, autoimmunity, transplantation rejection and the like.

In another preferred embodiment, at least one agent stimulates signaling of TNFRSF25 and induces proliferation of thymically induced, but not peripherally induced, Treg cells. The suppressive effects of the Treg cells can be monitored and the doses of the agent can be adjusted to maintain the suppressive effects in diseases or conditions wherein a decreased immune response is desired, for example, autoimmunity, transplantation rejection and the like.

In another preferred embodiment, at least one agent stimulates the signaling of TNFRSF25 and induces the proliferation of both thymically and peripherally induced Treg cells, where the cognate antigen recognized by the peripherally induced Tregs is known to be present. The suppressive effects of the Treg cells can be monitored and the doses of the agent can be adjusted to maintain the suppressive effects in diseases or conditions wherein a decreased immune response is desired, for example, autoimmunity, transplantation rejection and the like.

In another preferred embodiment, one or a combination of agents can be administered to a patient to modulate their immune response. For example, a patient may receive one or more agents in a therapeutically effective dose as determined by the proliferation of CD4+FoxP3+ cells in a patient, or any other assay that measures the desired response. For example immunoassays, biomarker detection, FACS, immuno blots, hybridization, PCR etc. The Treg cells can be identified as, for example, CD4+FoxP3+ cells. In some aspects there is co-expression of CD103. Expression of CD103 by Tregs contributes to the retention of tissues within tissues. Agents known not to interfere with TNFRSF25 mediated Treg proliferation include rapamycin.

In another preferred embodiment, the agent modulating TNFRSF25 signaling comprises at least one of: an antibody, an aptamer, a ligand, small molecule, peptide, protein, oligonucleotide, polynucleotide, organic or inorganic molecule.

In one preferred embodiment, the agent is an agonist of TNFRSF25.

In another preferred embodiment, a method of suppressing an immune response in vivo comprises administering to a patient in need thereof, at least one agent which modulates tumor necrosis factor superfamily receptor 25 (TNFRSF25; TNFR25; DR3) mediated signaling function; and, inducing a suppressive regulatory T cell (Treg) expansion.

In another preferred embodiment, the agent modulates tumor necrosis factor superfamily receptor 25 signaling and inhibits the suppressive activity of CD4+FoxP3+ regulatory T cells.

In another preferred embodiment, a composition for modulating an immune response comprising an agent which modulates TNFRSF25 signaling. In one embodiment, the agent is administered to a patient so that suppressor Tregs suppress an immune response. In another preferred embodiment, the agent is administered to a patient in a dose or under conditions which abrogate the signal leading to an inhibition of suppressor Treg cells so that an immune response is mounted.

In another preferred embodiment, a method of treating cancer in vivo comprising administering to a patient in need thereof, at least one agent which modulates tumor necrosis factor superfamily receptor 25 (TNFRSF25; TNFR25; DR3) function signaling at doses and conditions which provide continual stimulation of the TNFRSF25 which abrogates the suppressive effects of the Treg cells an immune response to cancer can be induced.

In another preferred embodiment, modulation of immune cells and subsequent responses comprises a method of treating a patient with a disease such as for example, cancer, viral disease, or disease caused by any infectious organism wherein an anti-TNFR25 composition, is administered to a patient, and modulates the functions of the immune cells, for example, proliferation of a lymphocyte wherein that lymphocyte had been previously suppressed or attenuated, or in cases where the immune response is normal but the enhancement of the enhancement of the immune response results in more effective and faster treatment of a patient. Negative regulatory pathway, and not lack of inherent tumor immunogenicity (i.e., the ability of the unmanipulated tumors to stimulate protective immunity), play an important role in preventing the immune-mediated control of tumor progression. The therapeutic implication is that countering immune-attenuating/suppressive regulatory circuits contributes to successful immune control of cancer and is as, if not more, important than developing potent vaccination protocols.

Tumor vaccines: As such, TNFR25 agonists are effective biological response modifiers, in for example, for tumor vaccines because they boost T cell activation and the cellular immune response to a tumor specific antigen, whereas TNFR25 antagonists block or inhibit T cell activation. Therefore, another aspect of the invention relates to methods and therapeutic agents that increase the effectiveness of a tumor vaccine.

Tumor vaccines attempt to the use of elements of the body's natural immune system to fight cancer. Tumor vaccines contain one or more tumor specific antigens and may contain an adjuvant and biological response modifiers. A tumor specific antigen is a polypeptide that is substantially limited to expression in or on tumor cells and which can be used to stimulate an immune response intended to target those tumor cells. Different types of vaccines are used to treat different types of cancer. For an antigenic composition to be useful as a vaccine, an antigenic composition must induce an immune response to the antigen in a cell or tissue. As used herein, an "antigenic composition" may comprise an antigen (e.g., a peptide or polypeptide), a nucleic acid encoding an antigen (e.g., an antigen expression vector), or a cell expressing or presenting an antigen.

The enhancement of the immune response to a vaccine or other antigenic stimulant can be measured by any conventional method, such as for example, proliferation assays, cytokine secretion, types of cytokines secreted, cytotoxic T lymphocyte assays, ELISAs, RIA and the like. The enhanced immune response can also be detected by monitoring the treatment. For example, in the case of treating cancer, an enhanced immune response could also be monitored by observing one or more of the following effects: (1) inhibition, to some extent, of tumor growth, including, (i) slowing down (ii) inhibiting angiogenesis and (ii) complete growth arrest; (2) reduction in the number of tumor cells; (3) maintaining tumor size; (4) reduction in tumor size; (5) inhibition, including (i) reduction, (ii) slowing down or (iii)

complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

In another preferred embodiment, the anti-TNFR25 can be administered as a vector construct expressing anti-TNFR25 antibodies. In addition, the vector construct can contain nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the subject's immune system, including both antibody and cytotoxic T lymphocyte responses, to bring out the specific level of response needed to control or eliminate the infection or disease state. The polynucleotide can also encode a fusion product containing an antigenic polypeptide, for example, an anti-tumor antigen, anti-viral antigen and the like, and a co-stimulatory molecule, such as CTLA-4. Examples of suitable vectors comprise viral vectors which include polio virus, pox viruses such as vaccinia, canary pox, and fowl pox, herpes viruses, including catfish herpes virus, adenovirus-associated vector, and retroviruses. Exemplary bacterial vectors include attenuated forms of Salmonella, Shigella, *Edwardsiella ictaluri, Yersinia ruckerii,* and *Listeria monocytogenes. L. monocytogenes* may also be valuable as a research tool used to stimulate the expansion of Tregs in animals so that they can be harvested at a later time point with an increased yield of Tregs per animal.

Combination Therapies

In a preferred embodiment, the enhancement or up-regulation of an immune response can be combined with one or more therapies. The anti-TNFR25 antibody, for example, can be administered prior to, concurrently with, or after a course of treatment with one or more agents or methods of treatment.

In another embodiment, the TNFR25 compositions can be administered to autologous cells, allow the cells to expand and then re-infuse the cells into the patient.

The TNFR25 stimulating agents can be administered in a pharmaceutical composition, as a polynucleotide in a vector, liposomes, nucleic acids peptides and the like.

In another preferred embodiment, the TNFR25 stimulating agents can be administered with one or more or additional pharmacologically active agents. As used herein, the term "pharmacologically active agent" refers to any agent, such as a drug, capable of having a physiologic effect (e.g., a therapeutic or prophylactic effect) on prokaryotic or eukaryotic cells, in vivo or in vitro, including, but without limitation, chemotherapeutics, toxins, radiotherapeutics, radiosensitizing agents, gene therapy vectors, antisense nucleic acid constructs or small interfering RNA, imaging agents, diagnostic agents, agents known to interact with an intracellular protein, polypeptides, and polynucleotides.

The additional pharmacologically active agent can be selected from a variety of known classes of drugs, including, for example, analgesics, anesthetics, anti-inflammatory agents, anthelmintics, anti-arrhythmic agents, antiasthma agents, antibiotics (including penicillins), anticancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radio-pharmaceuticals, hormones, sex hormones (including steroids), time release binders, anti-allergic agents, stimulants and anoretics, steroids, sympathomimetics, thyroid agents, vaccines, vasodilators, and xanthines.

The additional pharmacologically active agent need not be a therapeutic agent. For example, the agent may be cytotoxic to the local cells to which it is delivered but have an overall beneficial effect on the subject. Further, the agent may be a diagnostic agent with no direct therapeutic activity per se, such as a contrast agent for bioimaging.

Chemotherapy: The TNFR25 compositions can be administered with chemotherapy. Administration of for example, anti-TNFR25 would likely result in the decreased need of chemotherapy, or if chemotherapy is still required or recommended, the doses would be lower, thereby alleviating some of the adverse side effects of these chemotherapeutic agents. Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferees inhibitors, transplatinum, 5-fluorouracil, vincristin, vinblastin and methotrexate, or any analog or derivative variant of the foregoing.

Radiotherapy: The compositions can be combined with radiotherapy. Other factors that cause DNA damage and have been used extensively include what are commonly known as .gamma.-rays, X-rays, and/or the directed delivery of radioisotopes to tumor cells. Other forms of DNA damaging factors are also contemplated such as microwaves, proton beam irradiation (U.S. Pat. No. 5,760,395 and U.S. Pat. No. 4,870,287) and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapy: The anti-TNFR25 agents can be combined with other forms of immunotherapy. For example, in the context of cancer treatment, immunotherapeutics, generally, rely on the use of immune effector cells and molecules (e.g., monoclonal antibodies) to target and destroy cancer cells. Trastuzumab (HERCEPTIN™) or bevacizumab (AVASTIN™) is such an example. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and enhancement of tat immune effector response by for example, anti-TNFR25 antibody, would provide therapeutic benefit in the treatment of cancer.

The antigen specific immune response would target one or more tumor antigens and the administration of the TNFR25 compositions would enhance the immune response directed to these tumor antigens. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as MDA-7 enhance anti-tumor effects.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow. Preferably, human monoclonal antibodies are employed in passive immunotherapy, as they produce few or no side effects in the patient.

In active immunotherapy, an antigenic peptide, polypeptide or protein, or an autologous or allogeneic tumor cell composition or "vaccine" is administered, generally with a distinct bacterial adjuvant. In melanoma immunotherapy, those patients who elicit high IgM response often survive better than those who elicit no or low IgM antibodies. IgM antibodies are often transient antibodies and the exception to the rule appears to be anti-ganglioside or anti-carbohydrate antibodies.

In adoptive immunotherapy, the patient's circulating lymphocytes, or tumor infiltrated lymphocytes, are isolated in vitro, activated by, lymphokines such as IL-2 or transduced with genes for tumor necrosis. The TNFR25 compositions, for example anti-TNFR25 antibody, are administered or cultured with the cells which are then re-infused. To achieve this, one would administer to an animal, or human patient, an immunologically effective amount of activated lymphocytes in combination with anti-TNFR25 and, optionally, with an adjuvant-incorporated antigenic peptide composition. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond. The anti-TNFR25 can be administered to a patient, after re-infusion to the cells under a regimen that can be determined by the treating physician or nurse practitioner.

Immunosuppressants: The administration of one or more TNFRSF25 agents can be administered with one or more immunosuppressants where it is desired to maintain a suppressed immune response (e.g. autoimmune diseases). Examples of immunosuppressants, include without limitation: mycophenolic acid, azathioprine, cyclosporine A, FK506, FK520, Elidel; tacrolimus and sirolimus; minocycline; leflunomide; or methotrexate.

Surgery: Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well Other Agents: It is contemplated that other agents may be used in combination with the present invention to improve the therapeutic efficacy of treatment. These additional agents include immunomodulatory agents that affect the upregulation of cell surface receptors and GAP junctions, cytostatic and differentiation agents, the inhibition of cell adhesion, and the increase in sensitivity of the hyperproliferative cells to apoptotic inducers or other agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the enhancing abilities of the present invention. Increases in intercellular signaling by elevating the number of GAP junctions would increase the proliferative effects on desired cell populations.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, an enhancement of the immune response provides an alternative approach.

Another form of therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radio frequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Administration of Compositions

The pharmaceutical formulations and vaccines may be for administration by oral (solid or liquid), parenteral (intramuscular, intraperitoneal, intravenous (IV) or subcutaneous injection), transdermal (either passively or using ionophoresis or electroporation), transmucosal (nasal, vaginal, rectal, or sublingual), or inhalation routes of administration, or using bioerodible inserts and can be formulated in dosage forms appropriate for each route of administration.

For targeting a tumor cell in situ, the compositions described above may be administered to animals including human beings in any suitable formulation. For example, compositions for targeting a tumor cell may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

In some embodiments, the compositions or vaccines are administered by pulmonary delivery. The composition or vaccine is delivered to the lungs of a mammal while inhaling and traverses across the lung epithelial lining to the blood stream [see, e.g., Adjei, et al. *Pharmaceutical Research* 1990; 7:565 569; Adjei, et al. *Int. J. Pharmaceutics* 1990; 63:135 144 (leuprolide acetate); Braquet, et al. *J Cardiovascular Pharmacology* 1989; 13(sup5):143 146 (endothelin-1); Hubbard, et al. (1989) *Annals of Internal Medicine*, Vol. III, pp. 206 212 (al antitrypsin); Smith, et al. *J. Clin. Invest.* 1989; 84:1145-1146 (α 1-proteinase); Oswein, et al. "Aerosolization of Proteins", 1990; Proceedings of Symposium on Respiratory Drug Delivery II Keystone, Colo. (recombinant human growth hormone); Debs, et al. *J. Immunol.* 1988; 140:3482 3488 (interferon γ and tumor necrosis factor α); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al. See also U.S. Pat. No. 6,651,655 to Licalsi et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, NC); and the Spinhaler powder inhaler (Fisons Corp., Bedford, Mass.). All such devices require the use of formulations suitable for the dispensing of the therapeutic agent. Typically, each formulation is specific to the type of device employed and may involve the use of an appropriate propellant material, in addition to the usual diluents, adjuvants, surfactants and/or carriers useful in therapy. Also, the use of liposomes, microcapsules or microspheres, inclusion complexes, or other types of carriers is contemplated.

Formulations for use with a metered dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2 tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition or vaccine of the present invention may be administered in conjunction with one or more additional active ingredients, pharmaceutical compositions, or vaccines. The therapeutic agents of the present invention may be administered to an animal, preferably a mammal, most preferably a human.

Extended release systems: A first extended release system includes matrix systems, in which the agent is embedded or dispersed in a matrix of another material that serves to retard the release of the agent into an aqueous environment (i.e., the luminal fluid of the GI tract). When the agent is dispersed in a matrix of this sort, release of the drug takes place principally from the surface of the matrix. Thus the drug is released from the surface of a device, which incorporates the matrix after it diffuses through the matrix or when the surface of the device erodes, exposing the drug. In some embodiments, both mechanisms can operate simultaneously. The matrix systems may be large, i.e., tablet sized (about 1 cm), or small (<0.3 cm). The system may be unitary (e.g., a bolus), may be divided by virtue of being composed of several sub-units (for example, several capsules which constitute a single dose) which are administered substantially simultaneously, or may comprise a plurality of particles, also denoted a multiparticulate. A multiparticulate can have numerous formulation applications. For example, a multiparticulate may be used as a powder for filling a capsule shell, or used per se for mixing with food to ease the intake.

In a specific embodiment, a matrix multiparticulate, comprises a plurality of the agent-containing particles, each particle comprising the agent and/or an analogue thereof e.g. in the form of a solid solution/dispersion with one or more excipients selected to form a matrix capable of controlling the dissolution rate of the agent into an aqueous medium. The matrix materials useful for this embodiment are generally hydrophobic materials such as waxes, some cellulose derivatives, or other hydrophobic polymers. If needed, the matrix materials may optionally be formulated with hydrophobic materials, which can be used as binders or as enhancers. Matrix materials useful for the manufacture of these dosage forms such as: ethylcellulose, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble or hydrophilic binders or release modifying agents which can optionally be formulated into the matrix include hydrophilic polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials, which function as release-modifying agents include water-soluble materials such as sugars or salts. Preferred water-soluble materials include lactose, sucrose, glucose, and mannitol, as well as hydrophilic polymers like e.g. HPC, HPMC, and PVP.

In a specific embodiment, a multiparticulate product is defined as being processed by controlled agglomeration. In this case the agent is dissolved or partly dissolved in a suitable meltable carrier and sprayed on carrier particles comprising the matrix substance.

Dose: An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Therapeutic Treg Expansion In Vivo by TNFRSF25 Prevents Allergic Lung Inflammation The tumor necrosis factor superfamily (TNFSF) consists of at least 19 ligands and 30 receptors (TNFRSF) that are differentially expressed by both lymphoid and non-lymphoid cells. In CD3$^+$ T cells, TNFSF signals function usually in TCR-dependent ways to support various phases of an immune response including polarization, expansion, effector function, contraction, memory and death. TNFRSF25 (DR3, hereafter referred to as TNFR25) is one of the more recently discovered TNFSF members and is expressed primarily by CD4$^+$ and CD8$^+$ T and natural killer T (NKT) cells (Fang, L., Adkins, B., Deyev, V., and Podack, E. R. 2008. *J Exp Med* 205:1037-1048). TNFSF15 (TL1A), the ligand for TNFR25, is expressed by some endothelial cells and is rapidly induced on dendritic cells and macrophage/monocytes following TLR4 or FcγR signaling (Meylan, F., et al. 2008. *Immunity* 29:79-89; Prehn, J. L., et al. 2007. *J Immunol* 178:4033-4038). In vitro studies demonstrate that TNFR25 signaling on CD4$^+$, CD8$^+$ or natural killer T cells increases IL-2, IL-4 and IFNγ production subsequent to TCR activation or costimulation by IL-12 and IL-18 (Papadakis, K. A., et al. 2005. *J Immunol* 174:4985-4990). TNFR25 signaling also lowers the threshold of CD4$^+$ T cells to TCR induced proliferation in the absence of CD28 costimulation by an IL-2 dependent mechanism (Meylan et al. 2008; Migone, T. S., et al. 2002. *Immunity* 16:479-492).

Activation of TNFR25 by TL1A exacerbates disease pathology in experimental asthma, inflammatory bowel disease (IBD), rheumatoid arthritis (RA) and experimental autoimmune encephalomyelitis (EAE) (Pappu, B. P., et al. 2008. *J Exp Med* 205:1049-1062). In each of these studies, antigen dependent TNFR25 stimulation of Th1, Th2 or Th17 polarized and TCR activated effector T cells enhances the production of the relevant effector cytokines from each T helper subset. TNFR25 signals are not required for the differentiation of naïve CD4$^+$ T cells toward Th1, Th2 or Th17 lineages. In several of these reports, mouse models with genetic ablation of TNFR25 or TL1A (Pappu, B. P. et al., 2008; Takedatsu, H., et al. Gastroenterology 135:552-567. Bull, M. J., et al. 2008. *J Exp Med* 205:2457-2464) transgenic mouse models expressing a dominant negative TNFR25 or systemic antibody blockade of TL1A were studied. No immune abnormalities or disease susceptibilities have been observed in mouse models deficient in TL1A or TNFR25 or in autoaggressive disease models where the normal signaling of TL1A to TNFR25 is inhibited. Furthermore, in each of these reports expression of TNFR25 or TL produces a pro-inflammatory phenotype that appears more hazardous to the animal than in the absence of TNFR25 or TL1A. To date there have been no reports examining the role of TNFR25 on CD4$^+$FoxP3$^+$ regulatory T cells (Treg), although Treg may express TNFR25 (Pappu, B. P., et al. 2008. *J Exp Med* 205:1049-1062). Given the importance of Treg in preventing lethal autoimmunity), expression of TNFR25 by Treg and function of TNFR25 in the pathogenesis of multiple autoaggressive disease models we decided to study the role of TNFR25 on the function of Treg. This investigation revealed that TNFR25 is highly expressed by Treg but not FoxP3$^-$CD4$^+$ conventional T cells (Tconv). In vivo stimulation of TNFR25 in the absence of exogenous antigen using an agonistic antibody, clone 4C12, leads to the rapid and selective proliferation of natural Treg, but not Tconv, to 30-35% of all CD4$^+$ T cells within four days of 4C12 treatment and is dependent upon TCR engagement with MHC II and IL-2 signaling. Treg expansion by TNFR25 protects against lung inflammation upon airway antigen challenge of sensitized mice. These data demonstrate a novel role for TNFR25 as a regulator of Treg. This role can protect from disease pathogenesis in allergic asthma. Furthermore, in vivo expansion of natural Treg with TNFR25 agonists would provide a translatable method, as an alternative to IL-2- or ex vivo-based approaches, to facilitate the clinical use of Treg therapy in humans.

Materials and Methods:

Mice: Wild type C57BL/6 mice were purchased from Charles River Laboratories (Wilmington, Mass.). Foxp3-RFP reporter mice on a B6 background (Wan, Y. Y., and Flavell, R. A. 2005. *Proc Natl Acad Sci USA* 102:5126-5131)), FoxP3-GFP (Fontenot, J. D., et al. 2005. *Immunity* 22:329-341; Fontenot, J. D., Gavin, M. A., and Rudensky, A. Y. 2003. *Nat Immunol* 4:330-336) and CD45.1 SJL, MHC II$^{-/-}$ IL-2 receptor beta mutant, CD80/86$^{-/-}$ and CD4$^{-/-}$ mice were bred in our animal facility. TL1A$^{-/-}$ mice were purchased from Lexicon Genetics Inc. (The Woodlands, Tex.) and back-crossed into a C57BL/6 background by Speed Congenics. Mice were used at 6-12 weeks of age and were maintained in pathogen-free conditions at the UM Animal facilities. All animal use procedures were approved by the University of Miami Animal Care and Use Committee.

Antibodies and reagents. Commercial antibodies for use in flow cytometry were purchased from BD Pharmingen or eBioscience. The Armenian Hamster IgG Isotype control was bought from eBioscience. DTA-1 (α-GITR) was obtained from BioXCell, LG.3A10 (α-IL-27) from BioLegend and 158321 (α-4-1BB) from R&D Systems. Recombinant mouse IL-2 and anti-IL-2 monoclonal antibody, clone JES6-1A12, were purchased from eBioscience. Recombinant mouse IL-2/anti-IL-2 complex (IAC) was generated by incubating 10,000 units rmIL-2 with 5 μg JES6-1A12 for 15 minutes at 25° C. Armenian hamster hybridomas producing antibodies to mouse TNFR25 (4C12, agonistic) were generated as described previously (Fang, L., Adkins, B., Deyev, V., and Podack, E. R. 2008. *J Exp Med* 205:1037-1048). 4C12 (a-TNFR25) and OX-86 (α-OX40) were produced in hollow fiber bioreactors (Fibercell Systems, Frederick, Md.) and purified from serum-free supernatants on a protein G column (GE Healthcare, UK). Rapamycin (Rapamune, Wyeth) was used at 75 μg/kg/day as previously described (Araki, K., et al. 2009. *Nature* 460:108-112). Cyclosporin-A (25 mg/kg/day) FK506 (3 mg/kg/day) and Akt inhibitor V (Tricirbine, 1.5 mg/kg/day, or twice per day as indicated) were purchased from Calbiochem/EMD and administered by intraperitoneal injection.

Flow cytometry and cell sorting: Single cell suspensions were prepared from spleen and lymph nodes. 10$^6$ cells were pre-blocked with anti-mouse CD16/CD32 and stained with different antibody combinations. Intracellular staining was performed according to standard procedures. Flow cytometric analysis was performed on a Becton Dickinson FACS LSR II instrument and DIVA or FlowJo software. Cell sorting was done using a FACSAria cell sorter (BD) after enrichment of splenocytes for CD4$^+$ T cells using the EasySep Mouse CD4$^+$ T cell Pre-Enrichment Kit from Stem Cell Technologies.

Real-Time RT-PCR: Total RNA was extracted from flash-frozen colonic or lung tissue sections and reverse transcribed using the RNeasy Mini Kit and the QuantiTect Reverse Transcription Kit from QIAGEN, respectively. Real-time PCR was performed in duplicates on an ABI 7300 Light Cycler using TaqMan probes from Applied Biosystems. Samples were normalized to β-actin.

Adoptive transfer: For studies in FIGS. 2A and 2B, total CD4$^+$ cells were FACS sorted from FIR mice and the percentage of FoxP3$^+$RFP$^+$ cells was determined after sorting. Total CD4+ cells containing 10$^6$ FoxP3$^+$ cells were adoptively transferred (i.v.) into MHC or CD4$^{-/-}$ mice on day-2. On day 0, mice were treated with 4C12 antibody or isotype control. For studies in FIGS. 11A-11E, 2×10$^6$ FACS sorted CD4$^+$FoxP3$^-$ or CD4$^+$FoxP3$^+$ cells from CD45.2$^+$ FIR mice were adoptively transferred via intravenous injection into CD45.1 congenic SJL mice. One day later 10 μg of 4C12 was administered by intraperitoneal injection. The expansion of transferred cells was followed by FACS daily (starting after 3 days) in peripheral blood cells.

In vitro Suppression assays: 1×10$^5$ of CD4$^+$CD25− cells were plated in 96-well round-bottom plates and activated with 2 μg soluble anti-CD3 (2C11) antibody in the presence or absence of APCs (ratio 1:1) and CD4$^+$ FIR$^+$ regulatory T cells at different ratios. Control IgG, 4C12, DTA1 antibodies were added where indicated at a concentration of 10 μg/ml. Cultures were incubated for 72 h and pulsed with $^3$H-thymidine (1 μCi/well; Perkin Elmer, Waltham, Mass.) for the last 6 h. Incorporated isotope was measured by liquid scintillation counting (Micro Beta TriLux counter, Perkin Elmer).

Allergic Asthma Induction: Mice were sensitized by i.p. injection of 66 μg ovalbumin (crystallized chicken egg albumin, grade V; Sigma-Aldrich, St. Louis, Mo.) adsorbed to 6.6 mg alum (aluminum potassium sulfate; Sigma-Aldrich) in 200 μl PBS on day 0, with a i.p. boost on day 5. On day 12, mice were injected i.p. with either 20 μg anti-TNFRSF25 agonistic antibody (4C12) or 20 μg goat anti-hamster IgG isotype control (Jackson ImmunoResearch Laboratories Inc., Westgrove, Pa.) in 200 μl PBS. On day 16, mice were aerosol challenged with 0.5% ovalbumin (Sigma-Aldrich) in PBS for 1 hour using a BANG nebulizer (CH Technologies, Westwood, N.J.) into a Jaeger-NYU Nose-Only Directed-Flow Inhalation Exposure System (CH Technologies). On day 19, mice were sacrificed, lung perfused with PBS and bronchoalveolar lavages obtained. Lung lobes processed for RNA or for single cell suspensions made from lung homogenate for flow cytometry analysis, or for lung histology. Draining bronchial lymph nodes were also procured for subsequent RNA analysis as well as flow cytometry analysis. Quantification of periodic acid-Schiff (PAS) stained lung sections was performed using MacBiophotonics Image J software by color deconvolution (using the H PAS vector) followed by thresholding of images (color [2], set to 100) and counted using the nucleus counter (limits set to between 100-1000).

Statistical Analysis: All graphing and statistical analysis were performed using the ABI Prism program. Paired analysis was performed using the students T test. Multiple variable analysis was performed using one-way ANOVA and Tukey post-test. Significance is indicated as * ($p<0.05$),  ($p<0.01$) and * ($p<0.001$).

Results

TNFR25 is Highly Expressed by Regulatory T Cells: Prior to this study, there have been no reports demonstrating a function for TNFR25 on CD4$^+$FoxP3$^+$ regulatory T cells (Treg). To confirm whether there was expression of TNFR25 by Treg, FoxP3$^-$CD4$^+$ (Tconv) and Treg were single-cell sorted from FoxP3 reporter mice to over 99% purity and subsequently analyzed by flow cytometry for expression of TNFR25 as well as GITR (TNFRSF18), OX40 (TNFRSF4, CD134) and 4-1BB (TNFRSF9, CD137). Sorting of live Treg was made possible by use of FoxP3-reporter mice (FIR mice) expressing a red fluorescent protein knock-in transgene from a bicistronic construct under the FoxP3 promoter. This analysis revealed that while TNFR25, OX40, GITR and 4-1BB are all expressed by both Treg and Tconv, the greatest relative difference in expression levels was observed by very high expression of TNFR25 in Treg compared to low expression by Tconv (FIG. 1A). Without wishing to be bound by theory, the differential expression of TNFR25 between Treg and Tconv indicated that TNFR25 may play an important role in the function of Treg.

TNFR25 Stimulation Rapidly Expands Treg In Vivo: The generation of a TNFR25 agonistic antibody, clone 4C12 was described previously (Fang, L., Adkins, B., Deyev, V., and Podack, E. R. 2008. *J Exp Med* 205:1037-1048). By use of FIR mice the frequency and phenotype of the Treg population was continuously monitored in peripheral blood following treatment with the TNFR25 agonistic antibody, 4C12. Intraperitoneal (i.p) injection of 4C12 induced rapid and highly reproducible expansion of CD4$^+$FoxP3$^+$ Tregs in vivo (FIG. 1B). This expansion was maximal at 4 and 5 days post 4C12 injection, with FoxP3$^+$ Tregs comprising 30-35% of the total CD4$^+$ T cells in the peripheral blood at the peak of the response. 4C12 expanded Tregs persisted in the peripheral blood and all tissue sites examined for two weeks while slowly contracting to unstimulated levels. The site of injection did not play a role in this expansion, as demonstrated by equivalent Treg expansion following 4C12 injection either intraperitoneally, subcutaneously or intravenously. Treg expansion following 4C12 injection was dose-dependent with maximal responses seen with a dose of only 10 μg, corresponding to approximately 0.4 mg/kg body weight (FIG. 1B). Treatment of FIR mice with purified mouse TL1A-Ig fusion protein (100 μg) was found to induce Treg expansion with a similar magnitude and kinetic as treatment with the 4C12 antibody. Detection of RFP expression in FIR mice faithfully reports the presence of FoxP3 transcripts, however the possibility exists that it may not guarantee expression of FoxP3 protein because FoxP3 and RFP are independently translated from the FoxP3-RFP transcript. Therefore, expansion of CD4$^+$FoxP3$^+$ cells following 4C12 administration was confirmed in wild-type mice by staining with FoxP3 antibodies and in FoxP3-GFP knock-in reporter mice that express a FoxP3-GFP fusion protein.

Among Treg Expressed TNFR-Members TNFR25 Is Unique in Causing Treg Expansion: The TNFRSF members GITR and OX40 are expressed by Treg (FIG. 1A) and effect Treg activity and proliferation. It is thought that stimulation of Treg by 4-1BB can Modulate both the activity and proliferation of these cells. Furthermore, stimulation of CD4$^+$FoxP3$^-$ cells via TNFRSF member CD27 are thought to induce FoxP3 expression. Given the overlap between either functional suppression or induction of Tregs between TNFR25 and these other TNFSF members, Treg expansion was compared in vivo after stimulation of TNFR25, OX40, 4-1BB, GITR or CD27. In all cases well characterized agonistic monoclonal antibodies to the respective receptor were used to trigger specific signaling. These studies demonstrated that TNFR25 is unique among the TNFRSF members examined in its ability to selectively induce expansion of Tregs (FIG. 1C). It was recently reported that OX40-induced Treg expansion required depletion of IL-4, IL-6 and IFNγ (Ruby, C. E., et al. 2009. *J Immunol* 183:4853-4857). In contrast, TNFR25 induced Treg expansion in vivo required no additional manipulations.

MHC II and IL-2 Signals are Required for TNFR25 Induced Treg Proliferation: In vitro, Treg proliferation can be induced with various combinations of TCR-stimulating antibodies, antigen presenting cells and IL-2 signals. Induction of Treg proliferation in vitro was attempted in these studies using many different combinations of anti-CD3 and anti-CD28 antibodies, recombinant IL-2, TGF-β and retinoic acid with or without TNFR25 agonistic antibody, and in all cases TNFR25 stimulation failed to enhance Treg proliferation in vitro, indicating that additional signals were required (Table 1).

TABLE 1

Conditions tested in vitro using various purified lymphocyte populations (indicated) to examine requirements for TNFR25 induced Treg proliferation.

| Condition | Splenocytes | CD4+ | LN |
|---|---|---|---|
| 1. Unstim. | X | X | X |
| 2. Unstim. + 4C12 | X | X | X |
| 3. Unstim + 4C12 crossl. | X | | |
| 4. α-CD3 | X | X | X |
| 5. α-CD3 + 4C12 | X | X | X |
| 6. α-CD3 + 4C12 crossl. | X | | |
| 7. α-CD3 + TGF-β | X | X | X |
| 8. α-CD3 + TGF-β + 4C12 | X | X | X |
| 9. α-CD3 + RA | X | | |
| 10. α-CD3 + RA + 4C12 | X | | |
| 11. α-CD3 + RA + 4C12 crossl. | X | | |
| 12. α-CD3 + α-CD28 | X | X | X |
| 13. α-CD3 + α-CD28 + 4C12 | X | X | X |
| 14. α-CD3 + IL-2 | X | X | X |
| 15. α-CD3 + IL-2 + 4C12 | X | X | x |
| 16. α-CD3 + α-CD28 + IL-2 | X | | |
| 17. α-CD3 + α-CD28 + IL-2 + 4C12 | X | | |
| 18. α-CD3 + α-CD28 + TGF-β | X | | |
| 19. α-CD3 + α-CD28 + TGF-β + 4C12 | X | | |
| 20. α-CD3 + IL-2 + TGF-β | X | | |
| 21. α-CD3 + IL-2 + TGF-β + 4C12 | X | | |
| 22. α-CD3 + α-CD28 + IL-2 + TGF-β | X | | |
| 23. α-CD3 + α-CD28 + IL-2 + TGF-β + 4C12 | X | | |
| 24. One day in vivo + 4 days in vitro: IL-2 + 4C12 titration | x | | |

Figures 2A, 2B, 2C, 2D:
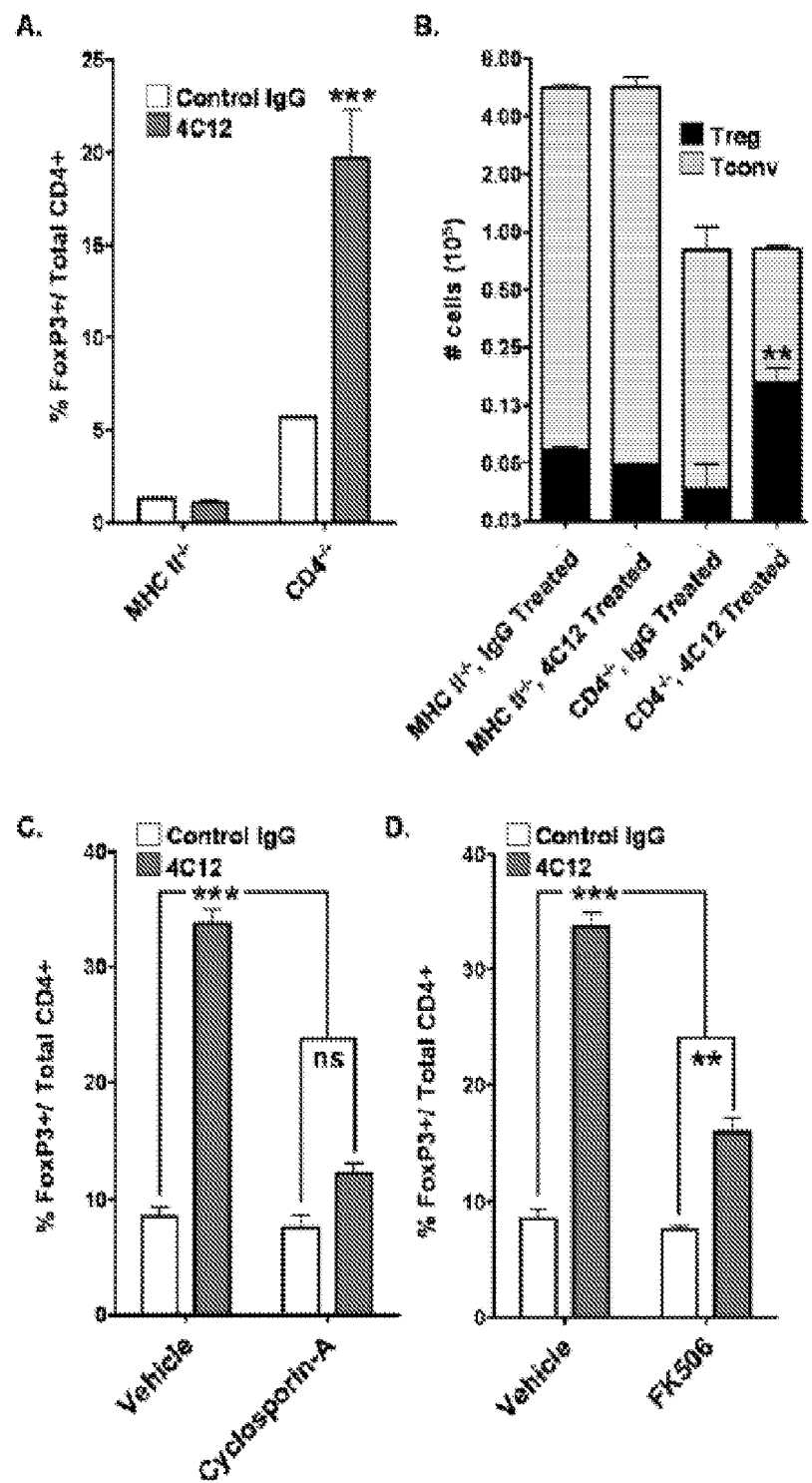
FIGS. 2A-2F show that TNFR25 induced Treg expansion requires TCR and IL-2 signaling. $CD4^+$ cells were highly purified by FACS sorting from FIR mice and adoptively transferred into $MHCII^{-/-}$ or $CD4^{-/-}$ mice. Following adoptive transfer, recipient mice were treated with either 4C12 or isotype control antibody and the percentage (FIG. 2A) and absolute number (FIG. 2B) of FoxP3-RFP positive cells was analyzed 4 days after antibody treatment. FIR mice were treated with cyclosporin-A (FIG. 2C) or FK506 (FIG. 2D) or a vehicle control from day-1 through day-4 by i.p. injection as described in the methods. Mice were treated with either 4C12 antibody or IgG control antibody and the proportion of FoxP3-RFP positive cells relative to total $CD4^+$ cells in the peripheral blood was analyzed on day 4. IL-2 receptor beta deficient mice (FIG. 2E) or $CD80/86^{-/-}$ mice (FIG. 2F) were analyzed for the proportion of $CD4^+FoxP3^+$ cells out of total $CD4^+$ splenocytes 4 days after treatment with either 4C12 or isotype control antibody, as compared to C57BL/6 control mice. These data are represented as the mean±S.E.M. of at least 2 independent experiments with ≥3 mice per group per experiment.  indicates p<0.01, * indicates p<0.001.
Figures 2E, 2F:
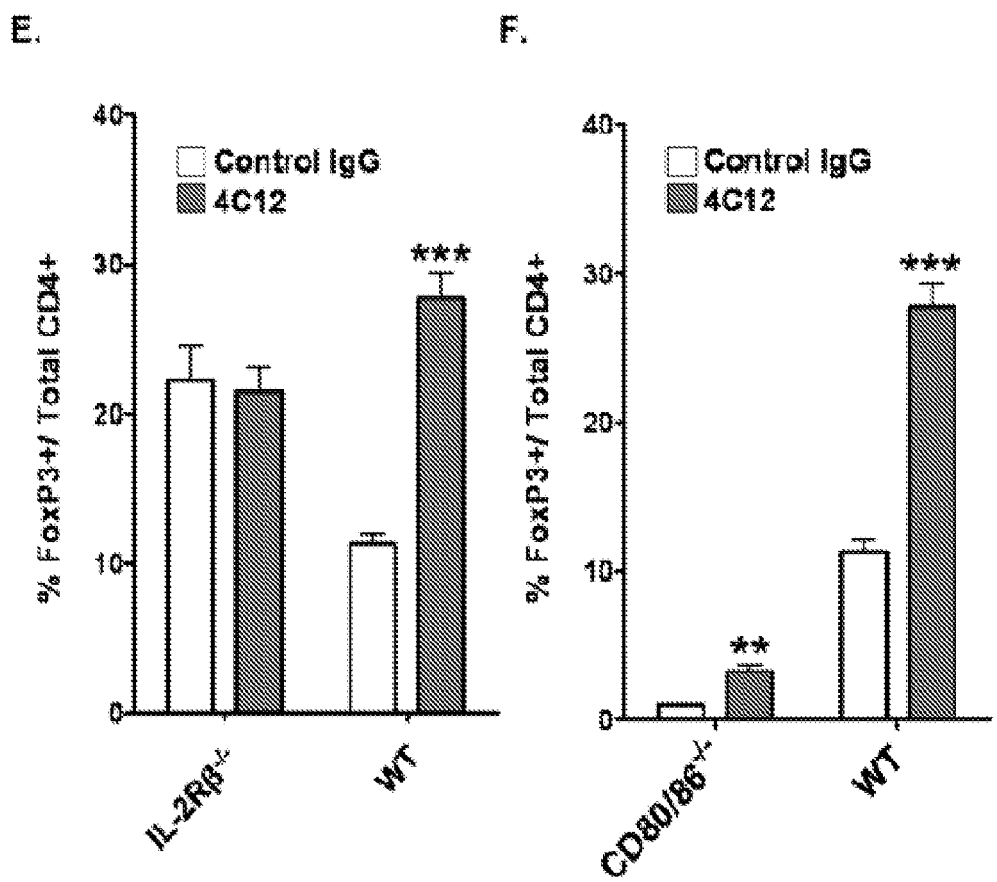

Since TNFR25 may influence the responsiveness of CD4+ T cells to TCR signals, the next experiments conducted were to determine whether TNFR25 induced Treg proliferation was dependent upon TCR signaling in vivo. MHC or CD4$^{-/-}$ mice were adoptively transferred with total CD4+ cells containing $10^6$ CD4+FoxP3+ cells purified from FIR mice. Because MHC II$^{-/-}$ mice are deficient in CD4+ T cells, it was decided to use CD4$^{-/-}$ mice as a control population to control for any homeostatic expansion that may occur following adoptive transfer into a CD4+ T cell depleted environment. Mice were treated with 4C12 or isotype control antibody 2 days after adoptive transfer and the percentage and absolute numbers of Treg were determined at days 4 and 6 after antibody injection (FIGS. 2A, 2B). These data demonstrate that although Treg expand to a similar degree in wild-type and CD4$^{-/-}$ mice, MHC II molecules are required for TNFR25 induced Treg proliferation in vivo. The percentage of adoptively transferred Treg in MHC II$^{-/-}$ mice was observed to be lower than in CD4$^{-/-}$ mice because MHC II$^{-/-}$ mice have a greater number of CD4+ cells at baseline than CD4−/− mice (FIG. 2A). A comparison of the absolute numbers of adoptively transferred Treg however (FIG. 2B), indicates that equivalent absolute numbers of Treg were recovered from the two groups. These studies demonstrate a requirement for MHC II signals in TNFR25 induced Treg proliferation, which indirectly implies that TCR signaling is required for Treg to become permissive to TNFR25 signaling, similar to TNFR25 signaling in Tconv cells. To provide additional evidence that TCR signals are required for TNFR25 induced Treg proliferation, mice were pre-treated with cyclosporine A or FK506 and Treg numbers were analyzed subsequent to treatment with the 4C12 or isotype control antibodies (FIGS. 2C, 2D). These studies demonstrate that, similar to what was observed in the absence of MHC II signals; TNFR25 triggering in the presence of cyclosporine A or FK506 fails to induce Treg proliferation. The requirement for cognate self-antigen in the MHC II is under further investigation, but such a requirement may provide additional explanation for Treg selectivity of TNFR25 (in addition to the selective expression of TNFR25 on Treg, FIGS. 8A-8C) in the absence of exogenous antigen.

It thought that TNFR25 signaling increases the responsiveness of Tconv to IL-2 signals subsequent to TCR signals in the absence of CD28 costimulation. Given the requirement for both MHCII and NFAT activation for TNFR25 induced proliferation of Treg (FIGS. 2A-2D) it was determined whether IL-2 or CD80/86 signals were additionally required. Treg expansion in mice expressing a non-functional IL-2 receptor beta chain (FIG. 2E) and CD80/86$^{-/-}$ mice (FIG. 2F) was determined 4 days after injection of 4C12. These data demonstrate that TCR and IL-2 receptor signaling, but not CD80 or CD86 costimulation is required for TNFR25 induced Treg expansion in vivo. Without wishing to be bound by theory, CD28 and CTLA-4 signaling in Treg may not be a requirement for TNFR25 induced proliferation. Furthermore, because combined TNFR25, TCR stimulation and IL-2 signaling fail to induce Treg proliferation in vitro, additional signals are required that are also under investigation.

Figures 3A, 3B, 3C:
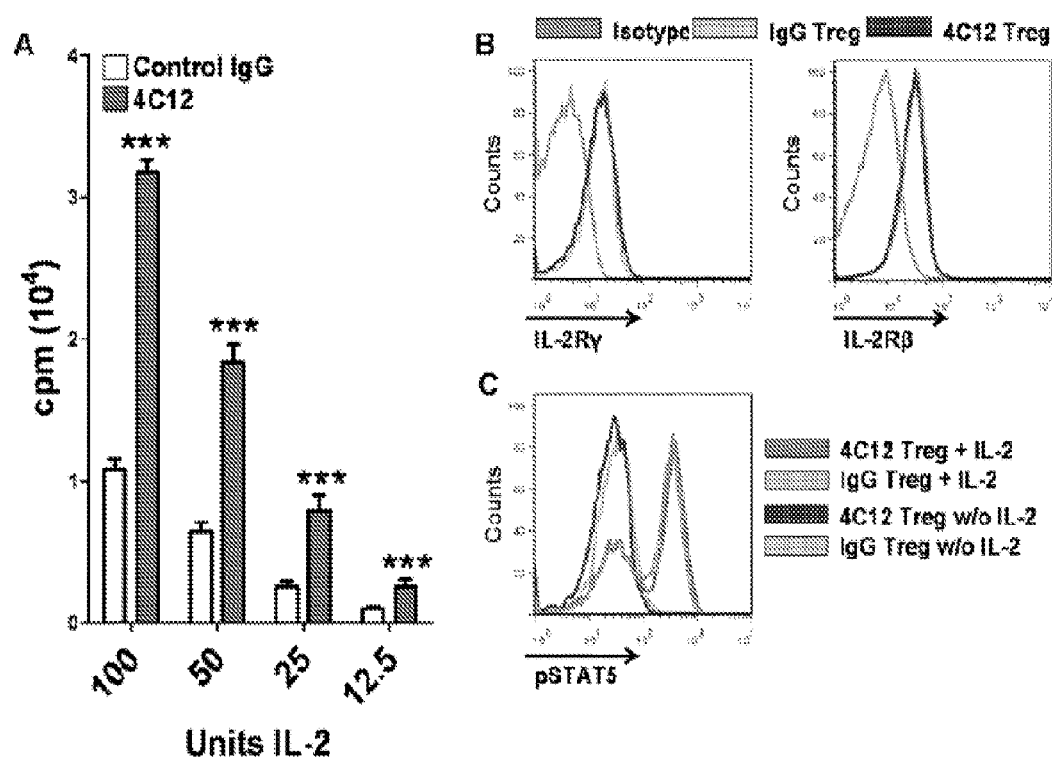
FIGS. 3A-3E show that TNFR25 expanded Treg are hyper-responsive to IL-2 and require Akt activation.
Figures 3D, 3E:
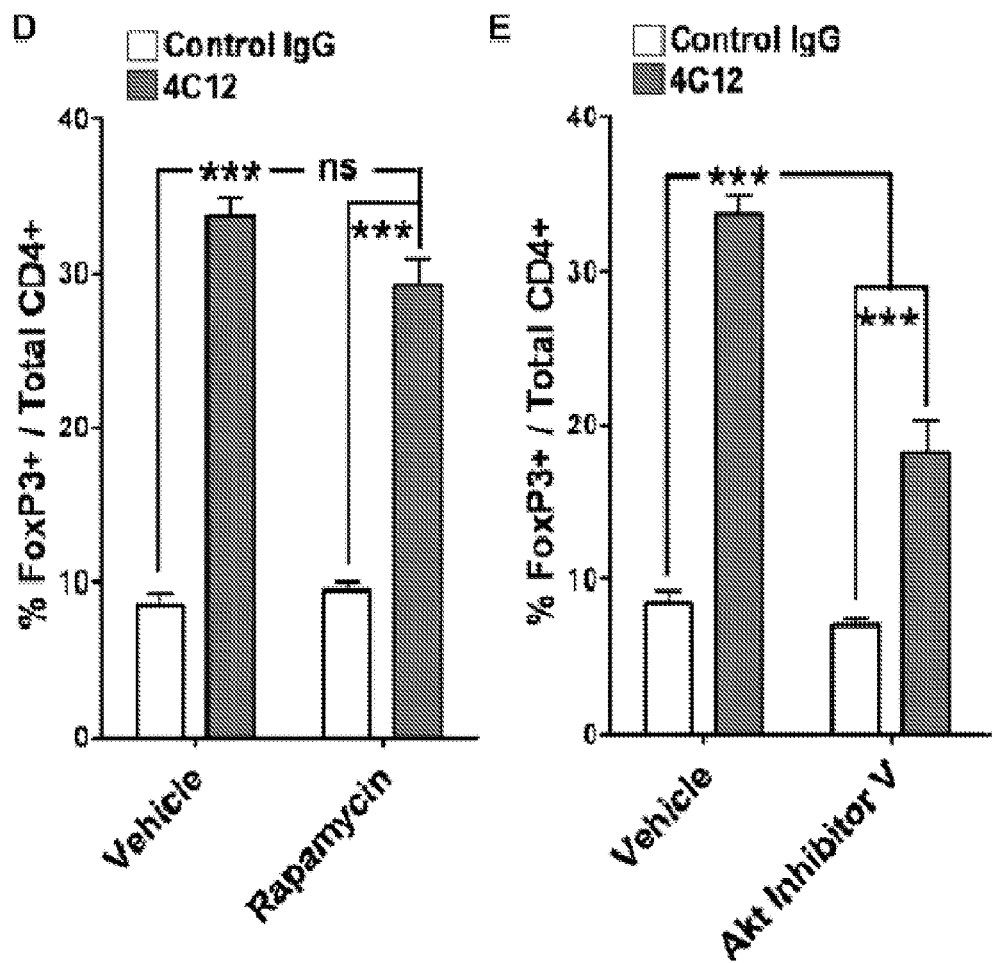

TNFR25 Stimulated Treg are Hyper-Responsive to IL-2 Induced Proliferation Ex Vivo: Although the requirements for TNFR25 induced Treg proliferation in vitro need further study, it was observed that Treg purified from mice treated with TNFR25 agonistic antibodies were hyper-responsive to IL-2 induced proliferation ex vivo (FIG. 3A). These data corroborate the importance of IL-2 signals in TNFR25 induced Treg expansion (FIG. 2E), and indicate that TNFR25 triggering induces Treg expansion by influencing the sensitivity of Treg to IL-2 signals. Several potential mechanisms were envisioned, that could explain this observation: 1) TNFR25 could increase the expression of IL-2 receptor subunits on Treg, 2) TNFR25 could enhance STAT5 activation in Treg, 3) TNFR25 could enhance mTOR activation in Treg and 4) TNFR25 could enhance PI3-kinase/Akt activation in Treg. To determine the expression of the IL-2 receptor alpha, beta and gamma chains, flow cytometry was performed on Treg undergoing expansion in vivo subsequent to treatment with the 4C12 antibody as compared to Treg isolated from mice treated with IgG control antibodies (FIG. 3B). These data demonstrate that while the expression of the IL-2 receptor alpha chain (CD25) actually decreases following exposure to 4C12 (FIG. 7A), expression of the beta and gamma chains (CD122 and CD132, respectively) remain unchanged on Treg isolated from mice treated with 4C12 and isotype control antibodies (FIG. 3B), effectively eliminating option (I) as a possibility. To determine whether phosphorylation of STAT5 was enhanced in 4C12 treated mice, Treg were isolated from mice treated 4 days previously with 4C12 or isotype control antibody and exposed to IL-2 ex vivo (10 ng/ml, 15 min). Subsequent staining of these Treg with phospho-specific antibodies demonstrated that neither STAT5 nor S6 phosphorylation were enhanced in Treg isolated from 4C12 treated mice as compared to control mice, effectively eliminating the second possibility (FIG. 3C). Subsequently, TNFR25 induced Treg proliferation in vivo was found to be unchanged in the presence of the mTOR inhibitor, rapamycin, eliminating the third possibility (FIG. 3D). Finally, to determine whether Akt signaling was required for TNFR25 induced Treg proliferation, mice were treated with TNFR25 agonistic antibodies or control antibody in the presence or absence of the Akt1/2/3 selective inhibitor, triciribine (Akt inhibitor V, AktiV). These studies demonstrated that selective inhibition of Akt activation was sufficient to inhibit TNFR25 induced Treg proliferation from 33.69±1.253% in vehicle treated controls to 22.43±1.352% (N=6) when treated once-daily with AktiV (data not shown, p<0.001) and to 18.20±2.117% (N=3) when treated twice-daily with AktiV (FIG. 3E, p=0.0003).

Figure 7A:
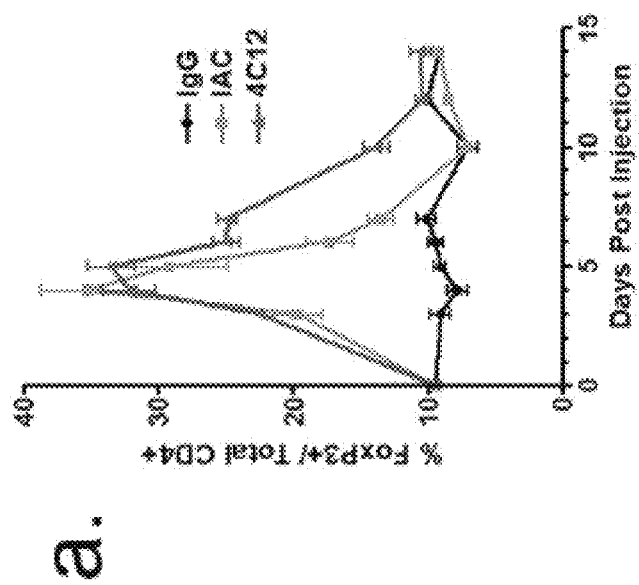
FIGS. 7A, 7B show the comparison of Treg expanded by treatment with 4C12 or recombinant IL-2/anti-IL-2 antibody complex (IAC).
Figure 7B:
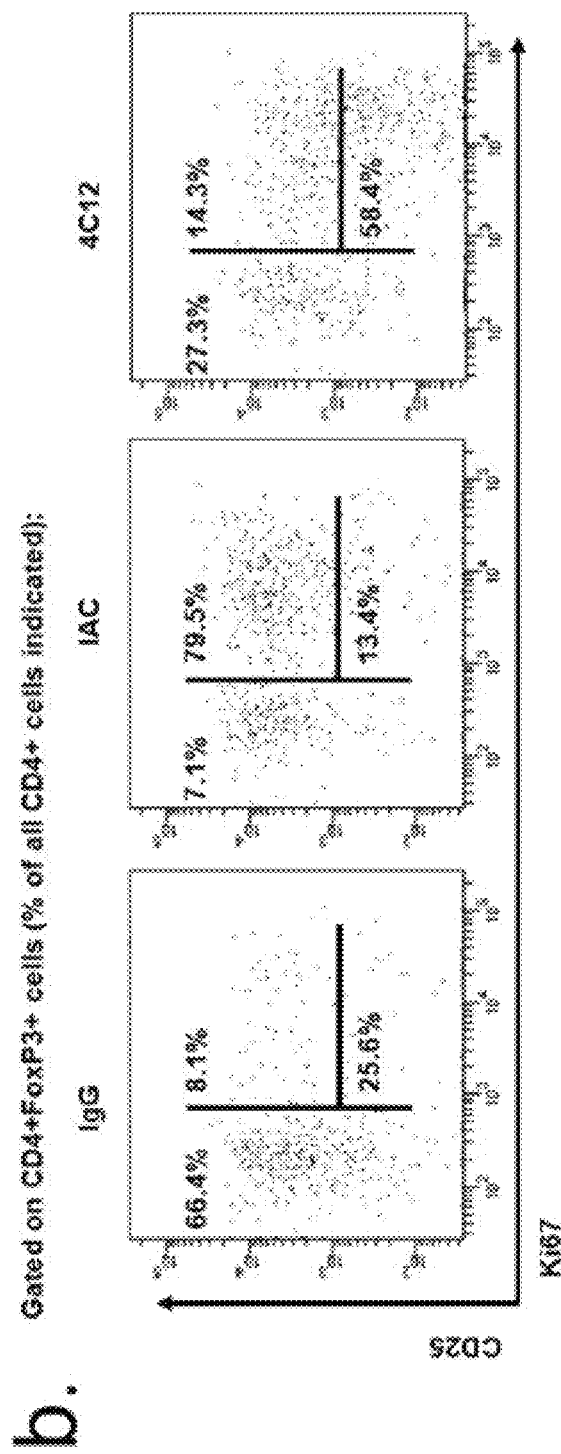

Comparison of TNFR25 or IL-2 Antibody Complex Induced Treg Expansion in Antigen Naïve Mice: The only other agent that selectively expands Treg in vivo was reported by Boyman et al, (*Science* 311:1924-1927, 2006) through use of a complex of recombinant IL-2 and a specific anti-IL-2 antibody (IAC), clone JES6-1A12. Thus, in vivo Treg expansion was directly compared following treatment with either 4C12 or IAC (FIG. 7A). This analysis demonstrates that the magnitude and kinetics of Treg expansion were similar following treatment with 4C12 or IAC in vivo. However the contraction of expanded Tregs was observed to be prolonged following treatment with 4C12 as compared to treatment with IAC. In contrast to TNFR25 expanded Treg, which expressed intermediate levels of CD25, IAC expanded Treg were observed to express high levels of CD25 (FIG. 7B). No other differences in expression of CD11a, CD28, CD45RA, CD62L, CD127, intra- or extra-cellular CTLA-4, OX40, PD-1, IL-17A or IFNγ were found by comparison of Treg expanded by 4C12 to Treg expanded by IAC.

Figures 4A, 4B, 4C, 4D, 4E:
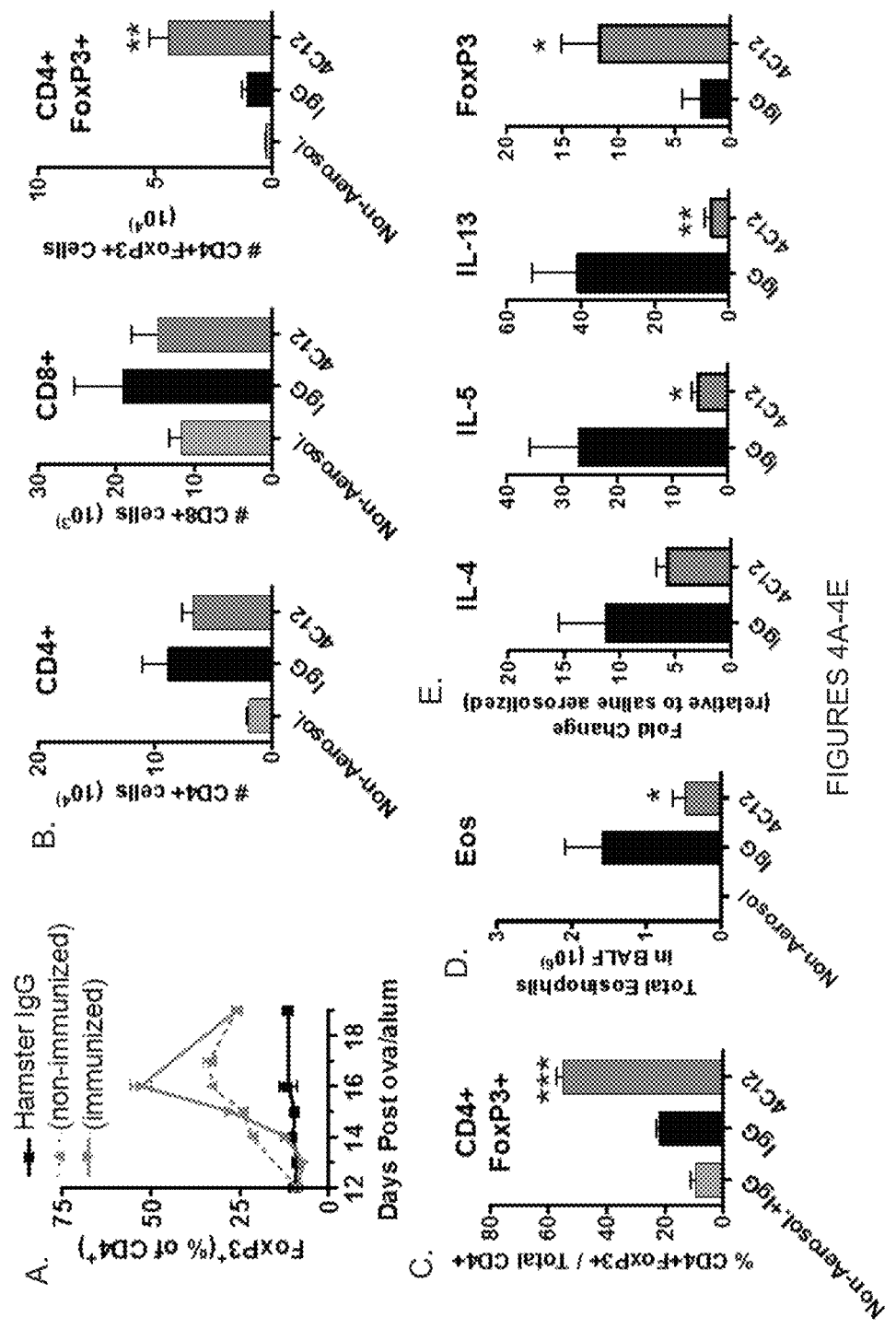
FIGS. 4A-4G show that in vivo Treg expansion by TNFR25 inhibits inflammation in allergic asthma. Allergic asthma was induced by immunization with ova/alum followed by aerosol challenge with ova/PBS as described in materials and methods.

In vivo Treg Expansion by TNFR25 Reduces Allergic Lung Inflammation: To determine whether 4C12 expanded Treg prevent inflammation in a disease model, it was tested whether this treatment could reduce inflammation in a well characterized model of allergic lung inflammation induced in ovalbumin/alum primed mice followed by airway ovalbumin challenge. Mice were primed with ovalbumin/alum on day 0 and 5 and then treated with 4C12 or hamster IgG on day 12. Four days later, at the time of maximal Treg expansion, the airways were challenged with ovalbumin aerosolized in PBS or a PBS saline control. Maximal expansion of Tregs was confirmed by monitoring Treg in the peripheral blood during this period (FIG. 4A). 4C12 induced Treg expansion following ovalbumin/alum sensitization was slightly delayed in the first two days, as compared to expansion in non-sensitized mice, but Tregs then rapidly expanded to a higher proportion (50-55%) of total CD4+ T cells by day 4 (FIGS. 4B, 4C). Mice were sacrificed three-days after aerosolization and bronchial alveolar lavage fluid (BALF), bronchial lymph nodes (bLN) and lung tissue were analyzed.

The total number of cells isolated from the lungs was unchanged between control or 4C12 treated animals. Consistent with this observation, the number of CD4+ and CD8+ T cells within the lungs was similar between control and 4C12 treated mice, however in 4C12 treated mice the number of Treg was significantly increased (FIG. 4B). Analysis of the composition of Treg within the lung tissue revealed that seven days after 4C12 administration (and 3 days after aerosolization) the frequency of Tregs in the lungs remained at 55% of all CD4+ T cells as compared to 22% in hamster IgG treated mice (FIG. 4C). It has been reported that the balance of Tconv to Treg is a better predictor of disease pathogenesis than merely the total number of Treg (Tang, Q., et al. 2008. *Immunity* 28:687-697; Monteiro, J. P., et al. 2008. *J Immunol* 181:5895-5903); the ratio of CD4+FoxP3− (Tconv) to Treg was determined in lung tissue (Table 2). To confirm that the phenotype of lung-infiltrating Treg was consistent with the phenotype of TNFR25-expanded Treg in disease-free mice, lung infiltrating Treg were analyzed and found to be indistinguishable from lung-infiltrating Treg isolated from IgG treated mice in expression of GITR, OX40, PD-1, CD44, CD62L and CD69.

TABLE 2

The total number of CD4+FoxP3− (Tconv), CD4+FoxP3+ (Treg) and the ratio of Tconv to Treg cells from total lung cells harvested as described for FIG. 10A-10E are shown. Cell numbers were calculated by multiplying the number of cells obtained in a single cell suspension of the left lung × the percentage of lymphoid gated cells out of total cells analyzed by flow cytometry × the percentage of Tconv or Treg cells within the lymphoid gated cell population.
4C12 decreases absolute $T_{conv}$ number and $T_{conv}:T_{reg}$ ratio

|  | IgG | 4C12 |
|---|---|---|
| # of $T_{conv}$/lung | 78,200 | 23,340 |
| # of $T_{reg}$/lung | 10,700 | 44,400 |
| $T_{conv}:T_{reg}$ ratio | 7:1 | 1:2 |

Consistent with analysis of lung tissue cells, the total number of cells isolated from BALF was significantly increased following aerosol challenge containing ovalbumin, but not saline aerosol control, in all conditions, but was markedly reduced by 4C12 treatment. The total number of eosinophils within the BALF roughly mirrored the total number of BALF cells, and pre-treatment with 4C12 was observed to significantly reduce the severity of airway eosinophilia (FIG. 4D).

Figures 4F, 4G:
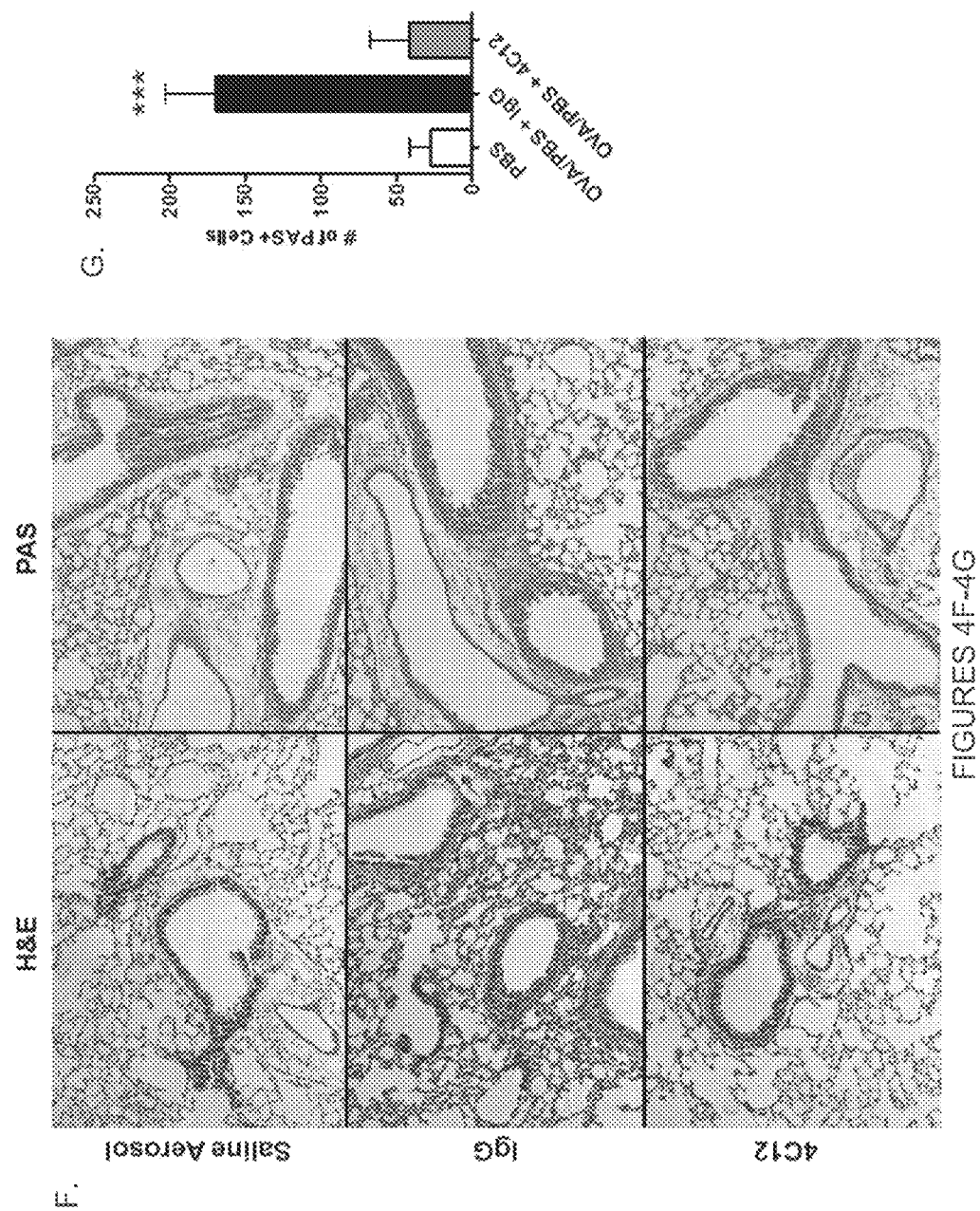

The pro-inflammatory cytokines IL-4, IL-5 and IL-13 have been strongly implicated in the pathogenesis of allergic lung inflammation. To determine whether expression of these cytokines was reduced by pre-treatment with 4C12, total RNA was extracted from flash-frozen lungs three days after aerosolization and analyzed by RT-PCR. This analysis demonstrates that the expression of IL-4, IL-5 and IL-13 among lung-infiltrating CD4+ cells is significantly reduced following treatment with 4C12, but remains elevated following treatment with isotype control antibody as compared to saline-aerosolized controls (FIG. 4E). As an additional control, the level of FoxP3 RNA expression was analyzed and mirrored the same relative proportions of FoxP3 expressing CD4+ cells as seen by flow cytometry (compare FIG. 4C to 4E). Lung tissue histology confirmed these findings, demonstrating reduced lymphocyte infiltration and airway mucus production following 4C12 treatment as compared to saline aerosolized controls (FIG. 4F and quantified in FIG. 4G).

TNFR25 Expands Treg without Activating or Expanding Tconv: To determine the phenotype of the 4C12-expanded Tregs, we analyzed CD4+FoxP3+ cells isolated from peripheral lymph nodes, mesenteric lymph nodes and spleens from mice that had been injected with 4C12 or IgG isotype control. 4C12 expanded Tregs were predominantly CD4+FoxP3+CD25 intermediate (int) cells and were found to be expanded in all secondary lymphoid organs analyzed (FIGS.

Figures 8A, 8B, 8C, 8D:
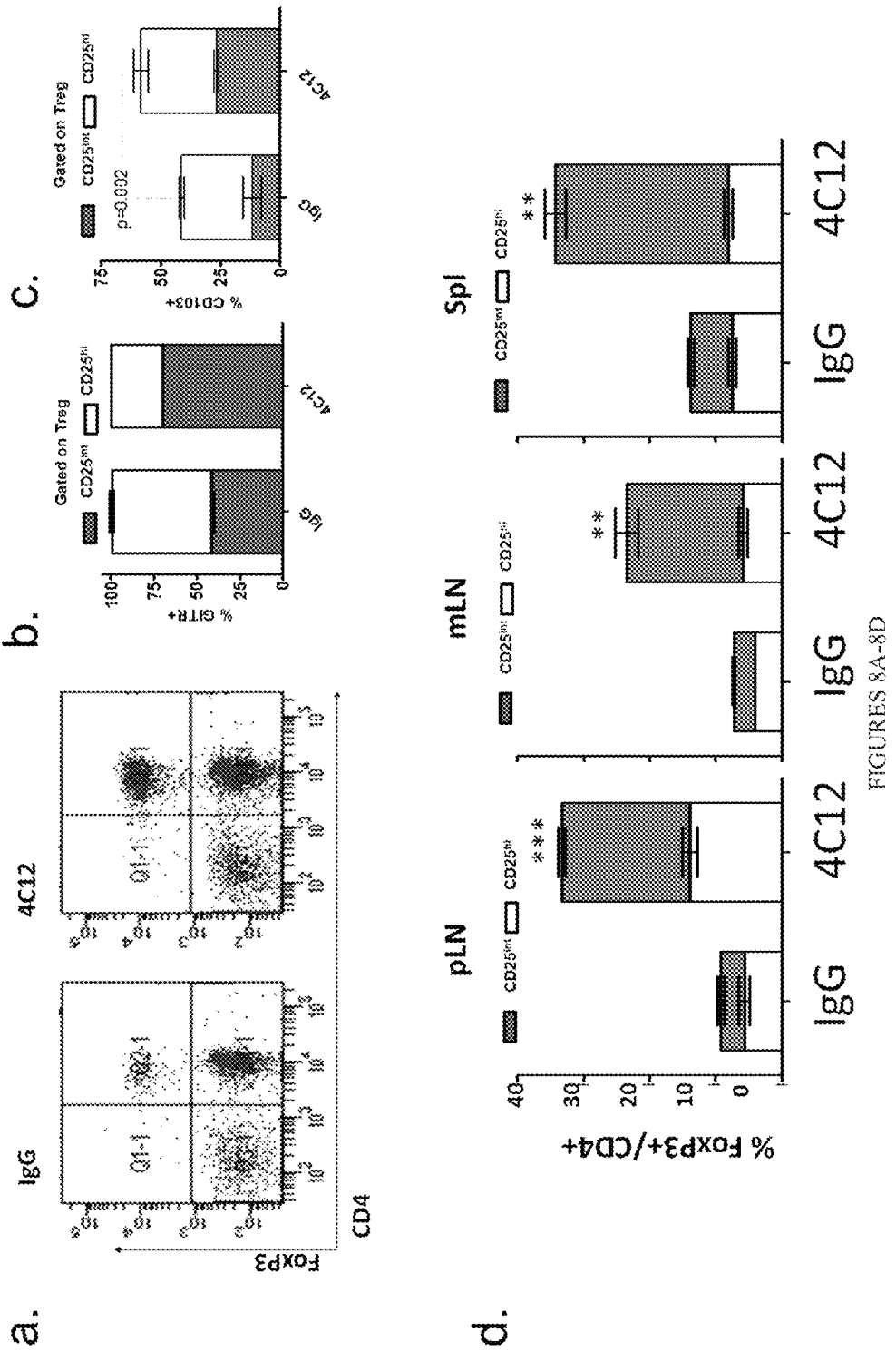
FIGS. 8A-8D show that 4C12 treatment induces Treg expansion in all tissues analyzed.

5A, 5B and FIGS. 8A, 8D). 4C12 treatment did not alter the expression of CD11a, CD28, CD45RA, CD62L, CD127, intra- or extra-cellular CTLA-4, OX40, PD-1, IL-17A or IFNγ by Treg. Although all CD4$^+$FoxP3$^+$ cells remained GITR positive following treatment with 4C12, the proportion of CD4$^+$FoxP3$^+$ cells that expressed GITR shifted in favor of the CD25 int subset following 4C12 treatment (FIG. 8B). The αEβ7 integrin is expressed by a highly suppressive subset of CD4$^+$FoxP3$^+$ that can be either CD25 positive or negative. Analysis of CD103 expression revealed increased expression of CD103 by 4C12 expanded Treg but not control Treg (FIG. 8C). Importantly, analysis of CD4$^+$FoxP3$^-$ cells and of CD8$^+$ cells following treatment with 4C12 revealed that TNFR25 signaling does not increase the absolute number or proportion of either of these cell populations. To determine whether treatment with 4C12 stimulated the proliferation of non-Treg cells, CD4$^+$ Tconv and CD8$^+$ T cells were stained with the proliferation marker, Ki67. This analysis illustrated that treatment with 4C12 in the absence of exogenous antigen did not increase Tconv or CD8$^+$ T cell proliferation. Moreover, staining of CD8$^+$ cells and FoxP3$^-$CD4$^+$ cells for CD44, CD62L and CD69 revealed no differences between 4C12 and IgG treated mice. Thus, TNFR25 signaling selectively expands Tregs without inducing expansion or activation of CD4$^+$ or CD8$^+$ effector cells in the absence of exogenous antigen.

Figures 5A, 5B, 5C, 5D, 5E, 5F, 5G, 5H:
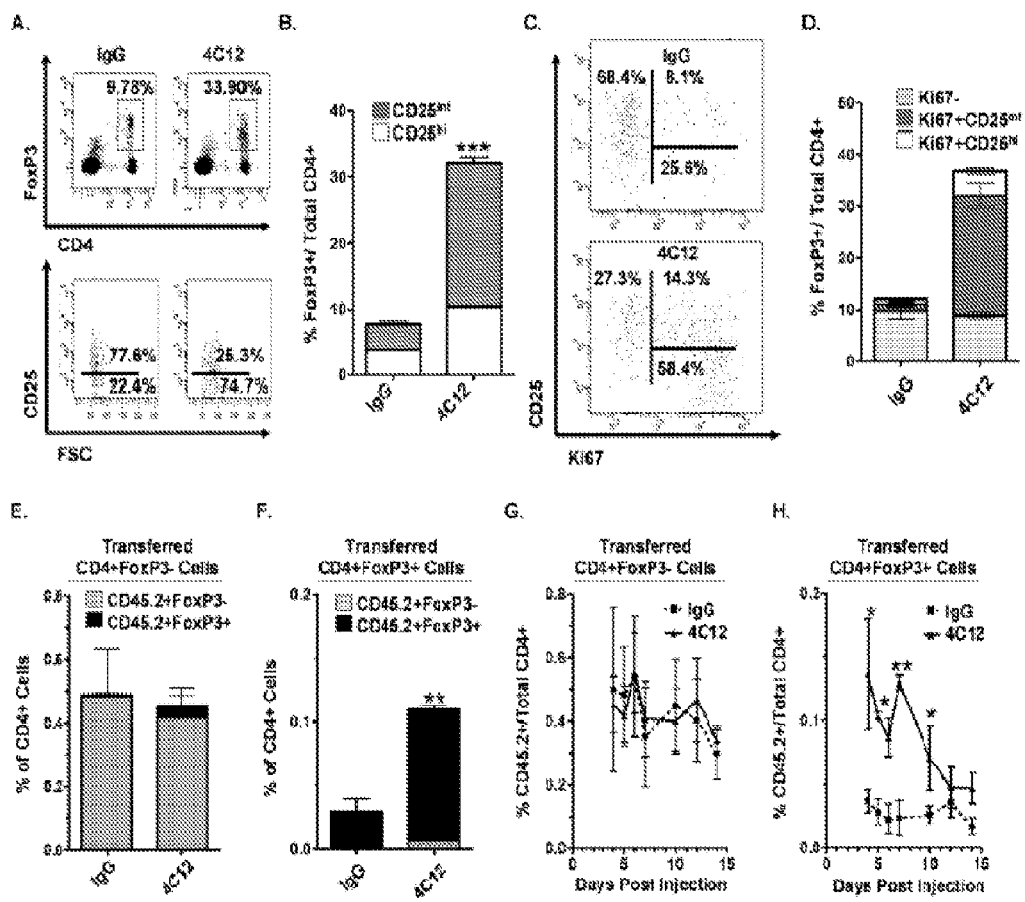
FIGS. 5A-5H show that TNFR25 stimulation leads to Treg expansion in vivo by inducing proliferation of existing CD4+FoxP3+ CD25int cells.

TNFR25 Stimulation Induces Proliferation of Natural Treg in Vivo: The increase in Tregs following 4C12 treatment could result either from de novo FoxP3 expression or from the proliferation of CD4$^+$FoxP3$^+$ cells. To differentiate between these two possibilities, the expression of the proliferative marker, Ki67, on CD4+ FoxP3+ cells was determined (FIGS. 5C, 5D). As the data showed that the increase in the ratio of CD4$^+$FoxP3$^+$CD25$^{int}$ cells relative to CD4$^+$FoxP3$^+$CD25$^{hi}$ cells, the majority of Ki67$^+$ cells was CD4$^+$FoxP3$^+$CD25$^{int}$ in mice that were treated with 4C12. A smaller proportion (~27%) of CD4$^+$FoxP3$^+$ cells did not stain for Ki67 (FIGS. 5C, 5D), and the majority of these cells were CD25$^{hi}$. It remains unclear whether the observed proliferation of CD25$^{int}$ cells following treatment with 4C12 resulted from the selective stimulation of CD25$^{int}$ cells or whether Treg were stimulated to proliferate regardless of CD25 expression, which was then reduced during proliferation.

Increased proliferation by CD4$^+$FoxP3$^+$CD25 int cells does not conclusively rule-out the possibility that TNFR25 signaling could stimulate de novo FoxP3 expression by CD4$^+$FoxP3$^-$ cells. To examine this possibility adoptive transfer experiments were performed by infusing highly purified (>99% purity) CD4$^+$FoxP3$^+$ or CD4$^+$FoxP3$^+$ cells from CD45.2$^+$ FIR mice into CD45.1 congenic B6/SJL mice. These studies allowed for the tracking of adoptively transferred CD45.2$^+$ cells following treatment with 4C12 in CD45.1$^+$ hosts and to monitor persistence, induction or silencing of FoxP3-RFP by adoptively transferred CD45.2$^+$ CD4$^+$ cells (FIGS. 5E-5H). It was deliberately chosen to perform these experiments in fully immunocompetent mice to avoid any complications that may arise from homeostatic expansion of Tregs following adoptive transfer into genetically or experimentally immunodeficient strains. Transfer of 2×10$^6$ sorted cells (FIG. 9A) into immunocompetent CD45.1$^+$ recipients was sufficient to detect a rare, but easily distinguishable, population of CD45.2$^+$CD4$^+$ cells in the peripheral blood for at least two weeks post adoptive transfer (FIGS. 5G, 5H). TNFR25 stimulation of recipient mice by 4C12 after adoptive transfer did not stimulate de novo FoxP3 expression by CD4$^+$FoxP3$^-$ cells (FIG. 5E) which remained at 0.5% frequency and FoxP3-RFP- regardless of 4C12 or control antibody treatment. The frequency of FoxP3$^+$RFP$^+$ cells after adoptive transfer of 2×10$^6$ cells was 0.04% of the CD4 cells in peripheral blood in mice treated with control antibody and increased to 0.11% in 4C12 treated mice (FIG. 5F) a three-fold increase of the frequency FoxP3$^+$RFP$^+$CD45.2$^+$ cells. This result is consistent with the extent of expansion of FoxP3$^+$ Treg by the TNFR25 agonistic antibody in non-transferred mice (FIG. 1B). The data indicate that 4C12 treatment selectively stimulates the proliferation of CD4$^+$FoxP3$^+$ cells, which maintain FoxP3 expression following expansion (FIG. 5F). The data show that TNFR25 signaling stimulates primarily increased proliferation of CD4$^+$FoxP3$^+$CD25$^{int}$ cells resulting in a systemic increase in Tregs. These studies also demonstrate that while the adoptively transferred CD4$^+$FoxP3$^-$ cells do not expand at any time following 4C12 treatment (FIG. 5G), the expansion of adoptively transferred CD4$^+$FoxP3$^+$ cells follows similar kinetics as the expansion and contraction of endogenous Tregs in FIR mice (compare FIG. 5H to FIG. 1B). Importantly, the adoptively transferred CD4$^+$FoxP3$^+$ cells maintain FoxP3 expression both during and after expansion, suggesting that the observed contraction of the expanded Treg pool results from cell death rather than from loss of FoxP3 expression (FIGS. 5F, 5H). If the expanded pool of adoptively transferred CD45.2$^4$CD4$^+$FoxP3$^+$ cells were losing FoxP3 expression at any point throughout the course of the experiment, the fraction of CD4$^+$FoxP3$^-$ cells within the CD45.2$^+$CD4$^+$ cells would have increased, however this did not occur. A small proportion of adoptively transferred CD4$^+$FoxP3$^-$ cells (<5%) were observed to exhibit FoxP3 expression (FIG. 5E) and a small proportion of transferred CD4$^+$FoxP3$^+$ cells (<5%) lost FoxP3 expression (FIG. 5F) over the course of the experiment. Such minor instabilities in FoxP3 expression likely explain these observations.

Figures 6A, 6B, 6C, 6D, 6E, 6F:
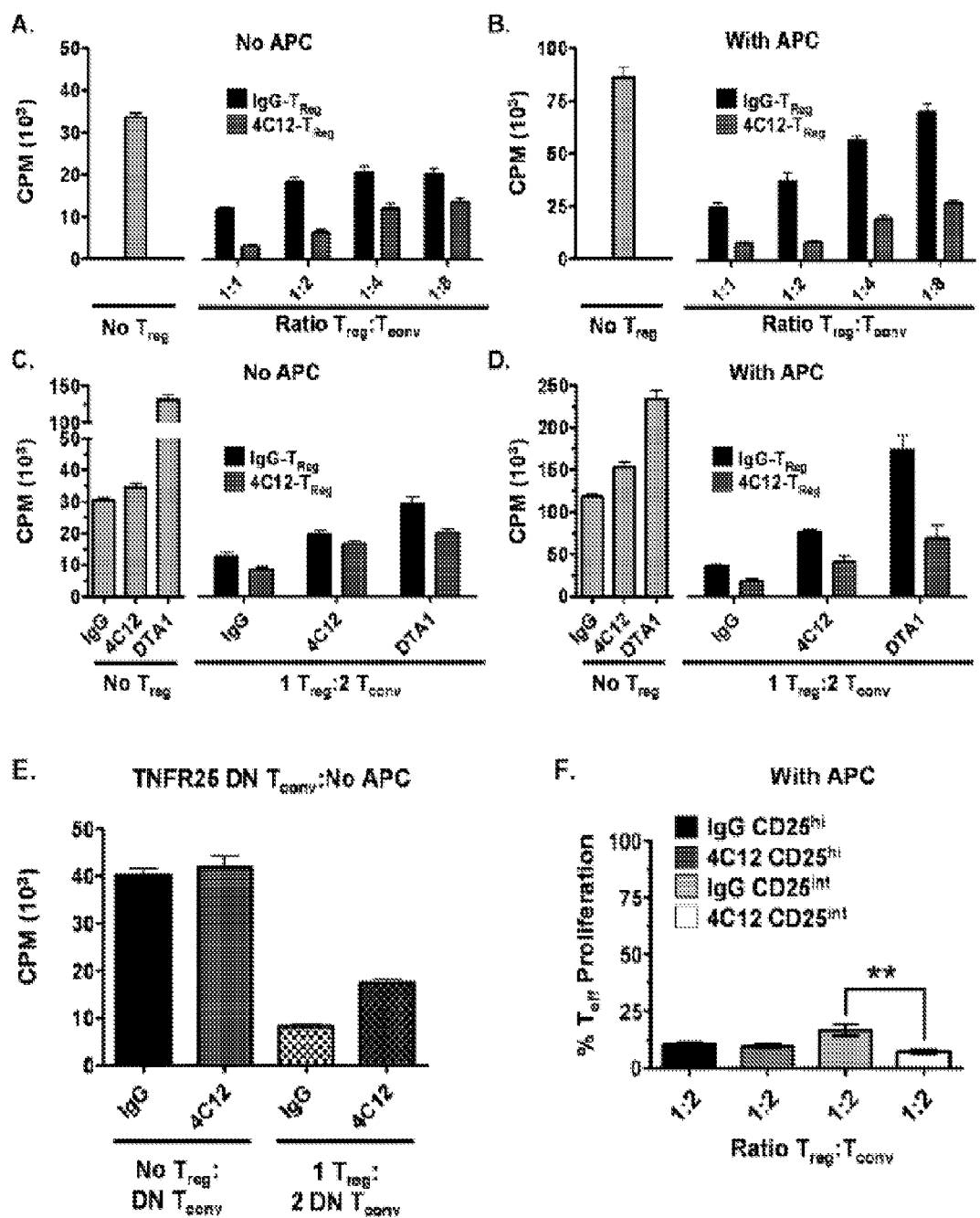
FIGS. 6A-6F show the suppressive activity of in vivo expanded Treg. $CD4^+FoxP3^+$ Treg cells were sorted from 4C12 and IgG isotype control injected mice on day 4 and subjected to a standard in vitro suppression assay using $CD4^+FoxP3^-CD25^-$ cells as Tconv and soluble α-CD3 (2 μg/ml) for 72 h (96-well, round bottom plate). The assay was performed in the absence (FIGS. 6A, 6C) or presence (FIG. 6B, 6D) of 1:1 antigen presenting cells (APCs) using different ratios of Treg:Tconv (FIGS. 6A, 6B).
Figures 9A, 9B:
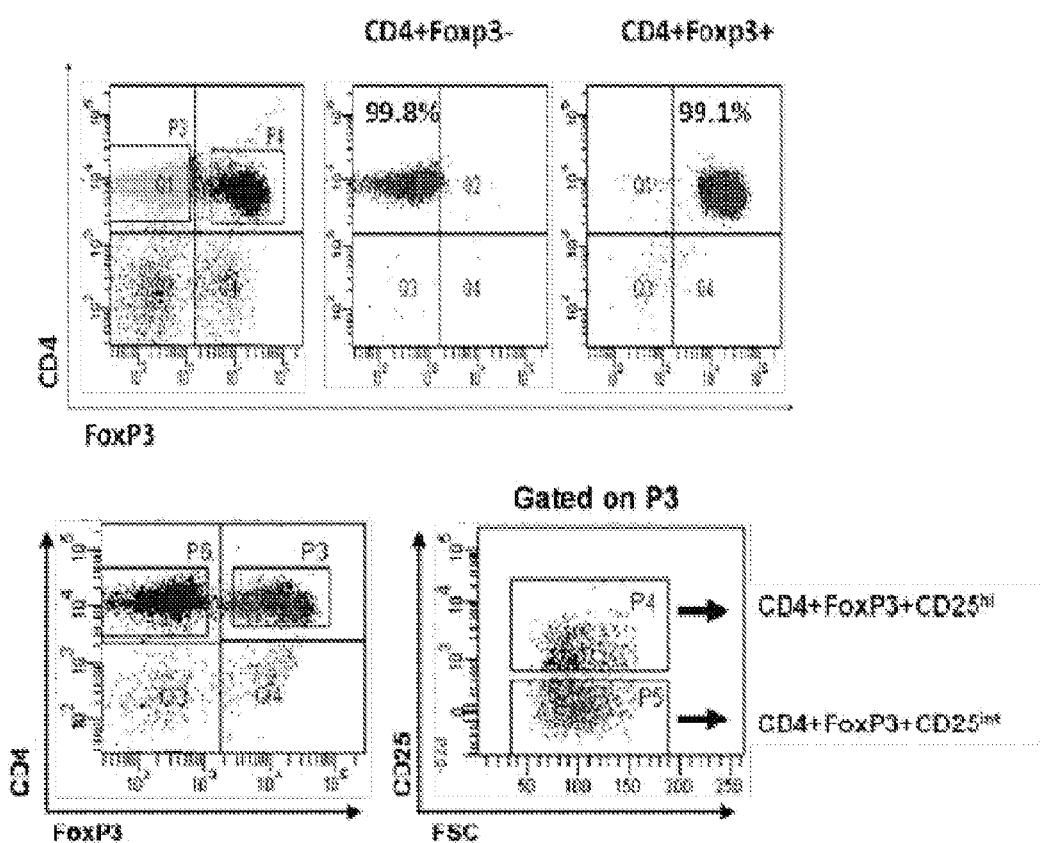
FIGS. 9A-9B show an example of sorting strategy and the results obtained.

TNFR25 Expanded Treg are Highly Suppressive Ex Vivo: To determine whether 4C12 expanded Tregs retain suppressive activity, Treg cells were purified from FIR mice four days after treatment with either 4C12 or IgG isotype control antibody (FIG. 8A). These Treg subsets were then used in a traditional proliferation assay. Purified Tregs from 4C12 treated mice suppressed proliferation of CD4$^+$CD25$^-$ cells to a greater degree than those from isotype control antibody treated mice (FIGS. 6A-6D). Suppression of Tconv proliferation by 4C12 expanded Treg was observed both in the presence and absence of antigen presenting cells (APC) in the in vitro suppression assay (FIG. 6A vs. 6B). To determine whether addition of 4C12 during the suppression assay modulated the suppressive activity of Treg, identical assays were performed as described (FIGS. 6A, 6B) in the presence of 4C12 or a GITR-agonistic antibody known to release Tconv from Treg-mediated suppression (clone DTA-1) or isotype control antibody (FIGS. 6C, 6D). The presence of agonistic TNFR25 or GITR antibodies partially restored Tconv proliferation, with both antibodies producing a similar effect in the absence of APC regardless of whether the Treg were obtained from 4C12 or IgG-isotype control treated mice (FIG. 6C). Interestingly, in the presence of APC, DTA-1 induced the proliferation of Tconv in the presence of Treg from IgG-isotype control treated mice to a greater extent than with Treg from 4C12 treated mice (FIG. 6D). The presence of APC did not significantly alter the partial restoration of Tconv proliferation in the presence of 4C12. Controls also demonstrated that the stimulatory effect of 4C12 on Tconv alone was minimal, and significantly less than the stimulatory effect of GITR on Tconv (FIGS. 6C, 6D). To further demonstrate that inhibition of Treg suppressive activity by 4C12 was specific to the effect of TNFR25 expressed by Treg and not Tconv, suppression assays were performed using transgenic Tconv expressing a dominant negative TNFR25 (FIG. 6E). These data demonstrate that the inhibition of Treg suppressive activity by TNFR25 signaling occurs under conditions where only Treg express a functional TNFR25, indicating that this effect is due to signaling by TNFR25 on Treg and not Tconv. Notably, Tregs expanded in vivo with 4C12 and then subjected to the in vitro suppression assays (FIGS. 6A-6B) are highly suppressive under conditions where the 4C12 antibody is no longer present. It is only when the 4C12 antibody is, maintained in the course of the suppression assay that partial inhibition of Treg suppressive activity is observed. Because 4C12 induced the proliferation of CD25' Treg, and in some studies the level of expression of CD25 is predictive of the suppressive activity of Treg, the suppressive activity of $CD25^{hi}$ and $CD25^{int}$ Treg sorted from mice following treatment with 4C12 or isotype control antibody was compared (FIG. 9B and FIG. 6F). The suppressive activity did not depend on the level of CD25 expression since $CD25^{hi}$ and $CD25^{int}$ Treg were both highly suppressive in the proliferation assay (FIG. 6F). Interestingly, the 4C12-expanded $CD25^{int}$ Treg had slightly greater suppressive activity than the $CD25^{int}$ Treg from the IgG-treated mice (FIG. 6F, bars 3-4). This finding indicates that the increased suppressive activity of 4C12-expanded Treg as compared to IgG-treated Treg (FIGS. 6A-6D) is at least partially attributable to the activity of $CD25^{int}$ cells.

Discussion:

Members of the TNF receptor family have been recognized as important costimulators of immune effector cell responses and as inducers of apoptosis. Here, TNFR25 was identified as a novel non-redundant function as regulator of T regulatory cells. TNFR25 mediates robust expansion of Treg in vivo in immune competent mice while at the same time partially restraining their suppressive activity. No other physiological signals, including those of other TNFR-family members have been reported to exert similar activity on Tregs. Further, the observation that TNFR25 signals induce Treg expansion with a similar magnitude and kinetic to the only other reported reagent to selectively expand Treg (IL-2/anti-IL-2 antibody complexes (Boyman, O., et al. 2006. *Science* 311:1924-1927), indicates that TNFR25 agonists may provide a translatable alternative to IL-2 based therapies for therapeutic use in humans.

Without wishing to be bound by theory, the TNFR25 and TL1A receptor: ligand pair is implicated in the generation of pathogenic inflammation in various disease models. Heretofore, there is not a single report which identifies a role for TNFR25 or TL1A in maintaining health or preventing disease, which indicates that such a role had evaded discovery. The availability of the TNFR25 agonistic antibody, 4C12, enabled for the first time the study of TNFR25 on various T-cell subsets in a setting where the temporal availability of TNFR25 signals, inflammatory signals and exogenous antigen could be independently controlled. The identification of a protective role for TNFR25 expanded Treg in allergic lung inflammation does not contradict previous studies implicating TL1A in the exacerbation of allergic lung inflammation because in the current studies TNFR25 signaling precedes antigen exposure whereas in previous studies TNFR25 signals follow antigen challenge. Rather, the differential expression of TNFR25 by Treg (high expression) as compared to Tconv (low expression) indicates that the sequence of exposure of T cells to antigen, costimulatory signals or TL may govern whether a particular inflammatory response is suppressed by Treg or induced by Tconv. In the current studies, treatment with TNFR25 agonists prior to airway antigen challenge induced the preferential accumulation of Treg, but not Tconv, within the airways and was associated with a reduction in production of IL-4, IL-5 and IL-13 as well as reduced eosinophilia and mucus production in the broncheo-alveolar space.

MHC II and IL-2 signals, but not CD80/86 costimulation, were needed for TNFR25 induced Treg proliferation. Although MHCII and IL-2 signals are required for TNFR25 induced Treg proliferation, provision of TCR and IL-2 signals are not sufficient to induce proliferation of Treg in vitro, indicating that additional signals may be required which are under further investigation. Although the requirement for MHCII strongly implicates the Treg-expressed TCR in TNFR25 induced Treg proliferation, these data are indirect. As additional evidence for a role of the TCR in this process, it was observed that TNFR25 triggering could not induce Treg proliferation in the presence of the NFAT inhibitors, cyclosporin-A or FK506; providing evidence that signaling events downstream of the TCR influence Treg proliferation. These data indicate that both Treg and Tconv may become permissive to TNFR25 signaling subsequent to TCR ligation, and that the Treg-selectivity of TNFR25 agonistic antibodies may be at least partially due to the availability of self-antigen under non-inflammatory conditions. Whether or not persistent TCR stimulation with self-antigen also contributes to the increased expression of TNFR25 in Treg as compared to Tconv, or whether this difference is maintained by unrelated signaling pathways is also not known.

Given that at least two additional receptor pathways (IL-2 receptor and TCR) are required for TNFR25 triggered Treg proliferation, the confluence of signaling pathways downstream of these receptors leading to Treg proliferation may be complex. A clue as to how these pathways may interact was provided by the observation that ex vivo, TNFR25-triggered Treg was hyper-responsive to IL-2 signals. It was subsequently determined that the PI3-kinase/Akt pathway provided a link downstream of the IL-2 receptor that is important for TNFR25 induced Treg proliferation. These data indicate that PTEN-mediated inhibition of the PI3-kinase/Akt pathway restricts the proliferation of Treg downstream of IL-2 signaling. Identification of MHCII, IL-2R, NFAT and Akt provide a tangible starting point for elucidating the signaling events downstream of TNFR25 triggering that culminates in Treg proliferation, but additional studies are to be conducted to elucidate the molecular mechanisms of cross-talk between these various pathways.

TNFR25 induced Treg expansion occurs with a similar kinetic and magnitude to Treg expansion induced by IAC, but results in an increase in the proportion of $CD25^{int}$ rather than $CD25^{hi}$ cells. The importance of this observation is unknown; however the increase in CD25 expression by Treg following exposure to IAC suggests a positive-feedback loop driven by the increased availability of IL-2. In the case of TNFR25 induced Treg expansion, the concentration of IL-2 is not manipulated, so the resulting decrease in CD25 expression by proliferating Treg may result from increased competition for endogenous IL-2 from an expanding Treg population. Interrogation of other Treg expressed surface markers revealed few differences between TNFR25 and IAC expanded Treg, although some, including GITR, fluctuated between the $CD25^{int}$ and $CD25^{hi}$ populations. The only marker analyzed that was consistently increased following 4C12 treatment was CD103, which contributes to the retention of Tregs within tissues.

The data complement recent data reporting roles for TNFR25 stimulation in the induction of inflammatory responses with the inhibition of Treg suppressive activity into a unified theory for the role of TL1A:TNFR25 interactions in both the induction and resolution of tissue inflammation. The precise mechanism by which TNFR25 stimulation induces both the proliferation of Tregs and inhibits their suppressive activity remain unclear, in part because the signaling pathways activated by TNFR25 signals are not well understood, and are under further investigation. In addition, it is unknown whether TNFR25-induced expansion of Treg in vivo is dependent upon the recognition of self-antigen and, similar to IAC, the conditions necessary for TNFR25-induced Treg expansion in vitro remain unclear and are under further investigation. Without wishing to be bound by theory, it is hypothesized that the identification of a requirement in vivo for MHC II to permit TNFR25 induced Treg proliferation indicates that TCR engagement is a general requirement for TNFR25 induced T cell costimulation, and that the Treg selectivity of TNFR25 in the absence of exogenous antigen is maintained both by the preferential expression of TNFR25 by Treg and by the availability of self-antigen presented by MHC II. The increased responsiveness of Tregs to TNFR25 stimulation from immunized versus non-immunized mice is also intriguing, and may indicate distinct functions for TNFR25 in primary versus secondary immune responses.

Regardless of the mechanism, due to the importance of TNFR25 signaling to the pathogenesis of a growing number of inflammatory diseases (asthma, IBD, EAE, RA) it is important to understand the spatio-temporal role which TNFR25 signaling exerts on various $CD4^+$ T cell subsets. It is highly likely that, similar to OX40, the temporal context of TNFR25 signaling may differentially guide inflammatory or regulatory immunity. The unique ability of TNFR25 signals to rapidly expand and transiently inhibit $CD4^+$ $FoxP3^+$ natural regulatory T cells may have important consequences for the treatment of autoimmune disease, chronic infection, transplantation and cancer.

Example 2

Therapeutic Treg Expansion In Vivo by TNFRSF25 Delays Acute Rejection of Allogeneic Hearts in a Heterotopic Heart Transplant Model To study tolerance induction by 4C12 expanded natural Treg a heterotopic heart transplant model was chosen which is well described for tolerance studies. Hearts from CBA/J mice ($H2^d$) were transplanted into the abdomen of C57BL/6 mice ($H2^b$) on day 0. On day-4, one group of mice was treated with the TNFRSF25 agonistic antibody, clone 4C12, by intraperitoneal injection (20 µg/mouse), with the other treated with hamster IgG isotype control antibody. At the time of transplant Treg expansion in the blood was confirmed in the 4C12 treated group. Allograft survival was monitored by palpating the heart manually and the pulse was graded on a scale from 0 to 4 (0=no pulse; 1=very mild; 2=mild; 3=moderate; 4=strong). Rejection is defined as cessation of palpable heart beat. At the time of rejection (=when the heartbeat stopped) the graft was removed, formalin fixed and submitted for pathologic examination. Loss of graft function within 48 h of transplant is considered a technical failure (<5%) and omitted from further analysis.

Example 3

Figures 10A, 10B, 10C, 10D, 10E:
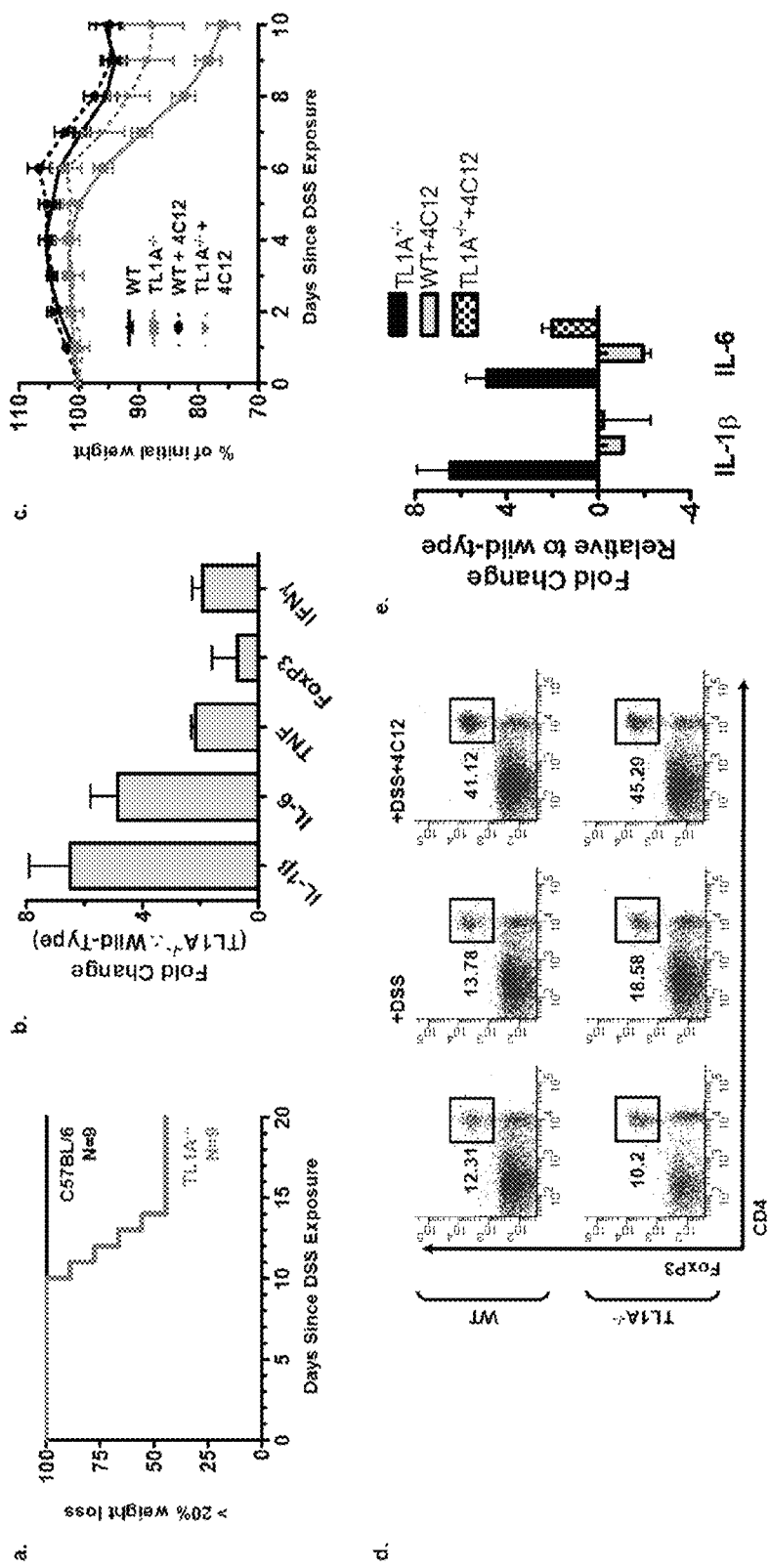
FIGS. 10A-10E demonstrate that TNFRSF25 agonists protect might from dextran-sodium sulfate induced colitis, a mouse model of Crohn's disease. C57BL/6 mice or TL1A knockout mice were provided with 3% dextran sodium sulfate (DSS) dissolved in drinking water ad libitum for 7 days. In some experiments, mice were treated on experimental day 0 with IgG isotype control antibody or with the TNFRSF25 agonistic antibody, clone 4C12. Weight was monitored daily beginning 4 days prior to provision of DSS (experimental day-4). On day-4, one group of mice was treated with the TNFRSF25 agonistic antibody, clone 4C12, by intraperitoneal injection (20 µg/mouse), with the other treated with hamster IgG isotype control antibody. Mortality was measured when animals lost ≥20% of starting body weight (FIG. 10A). In some experiments, animals were sacrifice at experimental day 5, and total RNA was prepared using the RNeasy miniprep kit (Qiagen) from flash-frozen, PBS-washed, colonic tissue. RNA was subsequently reverse transcribed (Quantitect RT, Qiagen) and cDNA was amplified by real-time PCR using Taqman (Applied Biosystems) probes for the indicated transcripts (FIG. 10B). Data are shown as the fold change in expression in TL1A knockout mice as compared to C57BL/6 control mice. The percentage body weight loss was monitored and plotted over the course of the study in each experimental group (FIG. 10C). In experiments where animals were sacrificed on experimental day 5 for RNA isolation, mesenteric lymph nodes were isolated for analysis by flow cytometry for the proportion of CD4+cells expressing the transcription factor FoxP3, indicative of the regulatory T cell pool (FIG. 10D). Finally, reverse transcription was performed using RNA isolated from the indicated treatment groups as described for FIG. 10B and subjected to RT-PCR for the indicated transcripts (FIG. 10E). Error bars indicate mean±S.E.M. for ≥3 mice per experiment and a minimum of 2 experiments per panel.
Figure 11:
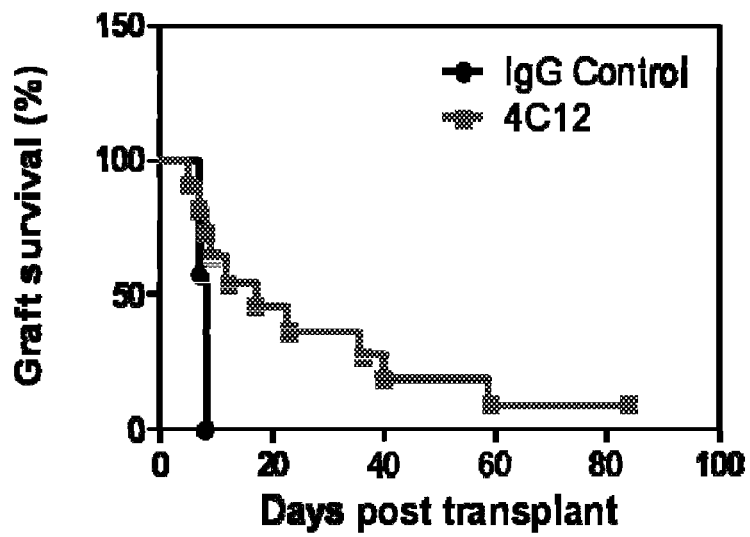
FIG. 11 demonstrates that TNFRSF25 agonists delay acute rejection of allogeneic hearts in a heterotopic heart transplant model in mice. To study tolerance induction by 4C12 expanded natural Treg a heterotopic heart transplant model was used which is well described for tolerance studies. Hearts from CBA/J mice (H2$^d$) were transplanted into the abdomen of C57BL/6 mice (H2$^b$) on day 0. On day-4, one group of mice was treated with the TNFRSF25 agonistic antibody, clone 4C12, by intraperitoneal injection (20 µg/mouse), with the other treated with hamster IgG isotype control antibody. At the time of transplant Treg expansion in the blood was confirmed in the 4C12 treated group. Allograft survival was monitored by palpating the heart manually and the pulse was graded on a scale from 0 to 4 (0=no pulse; 1=very mild; 2=mild; 3=moderate; 4=strong). Rejection is defined as cessation of palpable heart beat. At the time of rejection (=when the heartbeat stopped) the graft was removed, formalin fixed and submitted for pathologic examination. Loss of graft function within 48 h of transplant is considered a technical failure (<5%) and omitted from further analysis.
Figure 12:
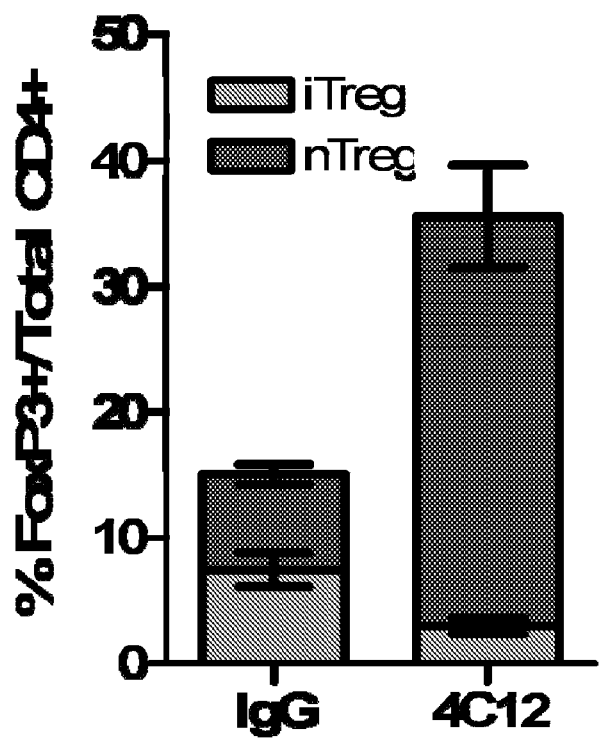
FIG. 12 demonstrates that TNFRSF25 agonists selectively expand natural; but not induced, T regulatory cells. CD4+FoxP3− T cells were isolated from mice expressing a FoxP3-RFP reporter gene and cultured in vitro for 5 days in the presence of IL-2, TGF-beta, anti-CD3 antibody and retinoic acid according to standard protocols. At the conclusion of the culture period the viable cells contained within the CD4+ population contained 70-85% CD4+FoxP3-RFP+ induced regulatory T cells (iTreg). These cells were purified by high-speed cell sorting. Concurrently, total CD4+ cells were purified from mice expressing a FoxP3-GFP reporter gene (these cells therefore contain a mixture of iTreg and so-called, thymically derived, natural regulatory T cells (nTreg)). iTreg (6×10$^5$ iTreg cells were mixed with total CD4+ cells isolated from FoxP3-GFP mice containing 8×10$^5$ Treg) and adoptively transferred (by intravenous injection) into CD4$^{-/-}$ recipient mice. After 2 days, CD4$^{-/-}$ recipient mice containing a mixture of RFP-positive iTreg and GFP-positive nTreg were treated with either 4C12 or IgG isotype control antibodies (20 µg/mouse, by intraperitoneal injection). Five days later, the proportion of RFP-positive iTreg and GFP-positive total Treg (containing the only source of nTreg) was determined by flow cytometry of isolated splenocytes (FIG. 12).

Therapeutic Treg Expansion In Vivo by TNFRSF25 Agonists Protect from Dextran-Sodium Sulfate Induced Colitis, a Mouse Model of Crohn's Disease C57BL/6 mice or TL1A knockout mice were provided with 3% dextran sodium sulfate (DSS) dissolved in drinking water ad libitum for 7 days. Weight was monitored daily beginning 4 days prior to provision of DSS (experimental day-4). On day-4, one group of mice was treated with the TNFRSF25 agonistic antibody, clone 4C12, by intraperitoneal injection (20 µg/mouse), with the other treated with hamster IgG isotype control antibody. Mortality was measured when animals lost ≥20% of starting body weight (FIG. 10A). In some experiments, animals were sacrificed at experimental day 5, and total RNA was prepared using the RNeasy miniprep kit (Qiagen) from flash-frozen, PBS-washed, colonic tissue. RNA was subsequently reverse transcribed (Quantitect RT, Qiagen) and cDNA was amplified by real-time PCR using Taqman (Applied Biosystems) probes for the indicated transcripts (FIG. 10B). Data are shown as the fold change in expression in TL1A knockout mice as compared to C57BL/6 control mice. The percentage body weight loss was monitored and plotted over the course of the study in each experimental group (FIG. 10C). In experiments where animals were sacrificed on experimental day 5 for RNA isolation, mesenteric lymph nodes were isolated for analysis by flow cytometry for the proportion of $CD4^+$ cells expressing the transcription factor FoxP3, indicative of the regulatory T cell pool (FIG. 10D). Finally, reverse transcription was performed using RNA isolated from the indicated treatment groups as described for FIG. 10B and subjected to RT-PCR for the indicated transcripts. Error bars indicate mean±S.E.M. for ≥3 mice per experiment and a minimum of 2 experiments per panel.

These data demonstrate that pre-treatment with a TNFRSF25 agonistic antibody leads to the expansion of $FoxP3^+$ regulatory cells within the gut, prevents weight loss and lethal inflammation in the colon, and prevents the expression of inflammatory cytokines including IL-1 beta and IL-6 within colonic tissue. Collectively, these data provide evidence that stimulation of TNFRSF25 can prevent lethal gut inflammation in a mouse model commonly used to mimic inflammation characteristic of Crohn's disease in humans.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of delaying acute rejection of a transplanted allograft in a subject, the method comprising the step of administering to the subject, prior to the subject receiving the transplanted allograft, a sufficient amount of a tumor necrosis factor receptor superfamily member 25 (TNFRSF25) agonist to increase the frequency of thymically-derived, natural T regulatory cells (nTreg) and for delaying rejection of the transplanted allograft, wherein the agonist is selected from the group consisting of: an agonistic anti-TNFRSF25 antibody and a soluble form of TL1A.

2. The method of claim 1, wherein the TNFRSF25 agonist is an antibody that specifically binds TNFRSF25.

3. The method of claim 2, wherein the antibody is a monoclonal antibody.

4. The method of claim 3, wherein the monoclonal antibody is of the IgG isotype.

5. The method of claim 1, wherein the administration is by injection.

6. The method of claim 1, wherein the method further comprises the step of assessing the function of the allograft following transplant.

7. The method of claim 1, wherein the method further comprises the step of monitoring CD4+FoxP3+ regulatory T (Treg) cell levels in the subject's blood.

8. The method of claim 1, wherein the method comprises monitoring Treg cell levels in the subject's blood prior to or at the time of transplant of the allograft.

9. The method of claim 1, wherein the method comprises monitoring the frequency of the nTreg in the subject's blood prior to or at the time of transplant of the allograft.

10. A method of delaying acute rejection of a transplanted allograft in a subject, the method comprising administering to the subject a sufficient amount of a TNFRSF25 agonist to delay rejection of the transplanted allograft, wherein the TNFRSF25 agonist is a soluble form of TL1A.

11. The method of claim 10, wherein the soluble form of TL1A is a TL1A fusion protein.

12. The method of claim 10, wherein the soluble form of TL1A is administered to the subject prior to the subject receiving the transplanted allograft.

13. The method of claim 12, wherein the administration of the soluble form of TL1A is effective for expanding nTreg in the subject.

14. The method of claim 13, wherein the method comprises monitoring the frequency of the nTreg in the subject's blood prior to or at the time of transplant of the allograft.

15. The method of claim 12, wherein the method comprises monitoring Treg cell levels in the subject's blood prior to or at the time of transplant of the allograft.

* * * * *

UNITED STATES PATENT AND TRADEMARK OFFICE
CERTIFICATE OF CORRECTION

PATENT NO. : 9,499,627 B2  
APPLICATION NO. : 13/388722  
DATED : November 22, 2016  
INVENTOR(S) : Eckhard R. Podack et al.

Page 1 of 1

It is certified that error appears in the above-identified patent and that said Letters Patent is hereby corrected as shown below:

In the Specification

Column 1, Lines 4-9, delete:
"CROSS REFERENCE TO RELATED APPLICATIONS
This application claims priority to U.S. provisional application No. 61/273,299, filed Aug. 3, 2009, which is incorporated herein by reference in its entirety."

On Column 1, Line 12, insert the following immediately after the "STATEMENT REGARDING FEDERALLY SPONSORED RESEARCH":
-- OR DEVELOPMENT
This invention was made with government support under grant numbers AI061807 and CA109094 awarded by the National Institutes of Health. The government has certain rights in the invention.
CROSS-REFERENCE TO RELATED APPLICATIONS --

Signed and Sealed this
Twenty-first Day of January, 2020

Andrei Iancu
*Director of the United States Patent and Trademark Office*